US012602112B2

(12) United States Patent
Alcaide et al.

(10) Patent No.: US 12,602,112 B2
(45) Date of Patent: *Apr. 14, 2026

---

(54) DETERMINING MENTAL STATES BASED ON BIOMETRIC DATA

(71) Applicant: Neurable, Inc., Boston, MA (US)

(72) Inventors: Ramses Eduardo Alcaide, Boston, MA (US); David Stanley, Cambridge, MA (US); Dereck Padden, Austin, TX (US); James Hamet, Somerville, MA (US); Adam Molnar, Boston, MA (US); Jamie Alders, Dover, MA (US); Jegan Candassamy, Lexington, MA (US); Arjun Daniel Srinivas, San Francisco, CA (US)

(73) Assignee: Neurable Inc., Boston, MA (US)

( * ) Notice: Subject to any disclaimer, the term of this patent is extended or adjusted under 35 U.S.C. 154(b) by 471 days.

This patent is subject to a terminal disclaimer.

(21) Appl. No.: 18/121,350

(22) Filed: Mar. 14, 2023

(65) Prior Publication Data

US 2023/0214018 A1    Jul. 6, 2023

Related U.S. Application Data

(63) Continuation of application No. 17/122,085, filed on Dec. 15, 2020, now Pat. No. 11,609,633.

(51) Int. Cl.
*G06F 3/01* (2006.01)
*A61B 5/00* (2006.01)
(Continued)

(52) U.S. Cl.
CPC .............. *G06F 3/015* (2013.01); *A61B 5/165* (2013.01); *A61B 5/291* (2021.01); *A61B 5/296* (2021.01);
(Continued)

(58) Field of Classification Search
CPC    G06F 3/15; G06F 9/542; G06F 21/32; G16H 50/20; G16H 20/30; G16H 20/70;
(Continued)

(56) References Cited

U.S. PATENT DOCUMENTS 4,669,477 A    6/1987  Ober
6,904,408 B1    6/2005  McCarthy et al.
(Continued)

FOREIGN PATENT DOCUMENTS

EP    3518129 B1    4/2021
JP    2003038454 A    2/2003
(Continued)

OTHER PUBLICATIONS

Office Action received in Japanese application No. 2023-536184, mailed on Oct. 8, 2024.
(Continued)

*Primary Examiner* — Christopher A Flory
(74) *Attorney, Agent, or Firm* — Young Basile Hanlon & MacFarlane, P.C.

(57) ABSTRACT

Various embodiments of an apparatus, methods, systems and computer program products described herein are directed to an Analytics Engine that receives one more signal files that include neural signal data of a user based on voltages detected by one or more electrodes on a set of headphones worn by a user. The Analytics Engine preprocesses the data, extracts features from the received data, and feeds the extracted features into one or more machine learning models to generate determined output that corresponds to at least one of a current mental state of the user and a type of facial gesture performed by the user. The Analytics Engine sends the determined output to a computing device to perform an action based on the determined output.

20 Claims, 14 Drawing Sheets

(51) Int. Cl.

| | | |
|---|---|---|
| *A61B 5/16* | (2006.01) | |
| *A61B 5/291* | (2021.01) | |
| *A61B 5/296* | (2021.01) | |
| *A61B 5/369* | (2021.01) | |
| *A61B 5/375* | (2021.01) | |
| *A61B 5/389* | (2021.01) | |
| *G01R 19/00* | (2006.01) | |
| *G05B 13/02* | (2006.01) | |
| *G06F 9/54* | (2006.01) | |
| *G06F 21/32* | (2013.01) | |
| *G10L 25/63* | (2013.01) | |
| *G16H 20/30* | (2018.01) | |
| *G16H 20/70* | (2018.01) | |
| *G16H 50/20* | (2018.01) | |
| *H04R 1/08* | (2006.01) | |
| *H04R 1/10* | (2006.01) | |

(52) U.S. Cl.

CPC .............. *A61B 5/369* (2021.01); *A61B 5/375* (2021.01); *A61B 5/389* (2021.01); *A61B 5/486* (2013.01); *A61B 5/6803* (2013.01); *A61B 5/742* (2013.01); *G01R 19/0084* (2013.01); *G05B 13/0265* (2013.01); *G06F 9/542* (2013.01); *G06F 21/32* (2013.01); *G10L 25/63* (2013.01); *G16H 50/20* (2018.01); *H04R 1/08* (2013.01); *H04R 1/1008* (2013.01); *H04R 1/1041* (2013.01); *G06F 2203/011* (2013.01); *G16H 20/30* (2018.01); *G16H 20/70* (2018.01)

(58) Field of Classification Search

CPC ......... A61B 5/165; A61B 5/291; A61B 5/296; A61B 5/369; A61B 5/375; A61B 5/389; A61B 5/486; A61B 5/6803; A61B 5/742

See application file for complete search history.

(56) References Cited

U.S. PATENT DOCUMENTS

| | | | |
|---|---|---|---|
| 7,747,323 | B2 | 6/2010 | Libbus et al. |
| 7,783,391 | B2 | 8/2010 | Jeong et al. |
| 10,877,444 | B1 | 12/2020 | Roach et al. |
| 11,269,414 | B2 * | 3/2022 | Alcaide .................. G06F 3/013 |
| 2005/0215916 | A1 | 9/2005 | Fadem et al. |

| | | | |
|---|---|---|---|
| 2005/0288954 | A1 | 12/2005 | McCarthy et al. |
| 2006/0004298 | A1 | 1/2006 | Kennedy et al. |
| 2006/0293921 | A1 | 12/2006 | McCarthy et al. |
| 2007/0106169 | A1 | 5/2007 | Fadem |
| 2007/0164985 | A1 | 7/2007 | Jeong et al. |
| 2012/0243729 | A1 | 9/2012 | Pasquero |
| 2013/0046206 | A1 | 2/2013 | Preminger |
| 2014/0126782 | A1 | 5/2014 | Takai et al. |
| 2014/0164095 | A1 | 6/2014 | Pradeep et al. |
| 2015/0033258 | A1 | 1/2015 | Klappert et al. |
| 2015/0077697 | A1 | 3/2015 | Gottardi et al. |
| 2015/0230020 | A1 | 8/2015 | Jeon et al. |
| 2015/0370333 | A1 | 12/2015 | Ataee et al. |
| 2016/0302686 | A1 | 10/2016 | Einarsson et al. |
| 2017/0339484 | A1 | 11/2017 | Kim |
| 2018/0107275 | A1 | 4/2018 | Chen et al. |
| 2018/0239430 | A1 | 8/2018 | Tadi et al. |
| 2020/0029881 | A1 | 1/2020 | Flood et al. |
| 2020/0064921 | A1 | 2/2020 | Kang et al. |
| 2020/0065569 | A1 | 2/2020 | Nduka et al. |
| 2020/0192478 | A1 | 6/2020 | Alcaide et al. |
| 2020/0268296 | A1 * | 8/2020 | Alcaide .................. G06F 3/013 |

FOREIGN PATENT DOCUMENTS

| | | |
|---|---|---|
| JP | 2004133794 A | 4/2004 |
| JP | 2005018167 A | 1/2005 |
| JP | 2005087486 A | 4/2005 |
| JP | 2006015046 A | 1/2006 |
| JP | 2008305107 A | 12/2008 |
| JP | 2016021259 A | 2/2016 |
| JP | 2018-504719 A | 2/2018 |
| JP | 2018139630 A | 9/2018 |
| JP | 2018186934 A | 11/2018 |
| JP | 2020530322 A | 10/2020 |
| KR | 20160107885 A | 9/2016 |
| WO | 2019099831 A1 | 5/2019 |
| WO | 2020075475 A1 | 4/2020 |

OTHER PUBLICATIONS

J. Kuffuor and B. Samanta, "Brain Computer Interface Using Motor Imagery and Facial Expressions to Control a Mobile Robot," SoutheastCon 2018, St. Petersburg, FL, USA, 2018, pp. 1-8, doi: 10.1109/SECON.2018.8479052.

Extended European Search Report received in European application No. 21907581.9, mailed on Sep. 17, 2024.

* cited by examiner

System Diagram

212

210

202
Headphones with
EEG & EMG
Electrodes

<u>300</u>

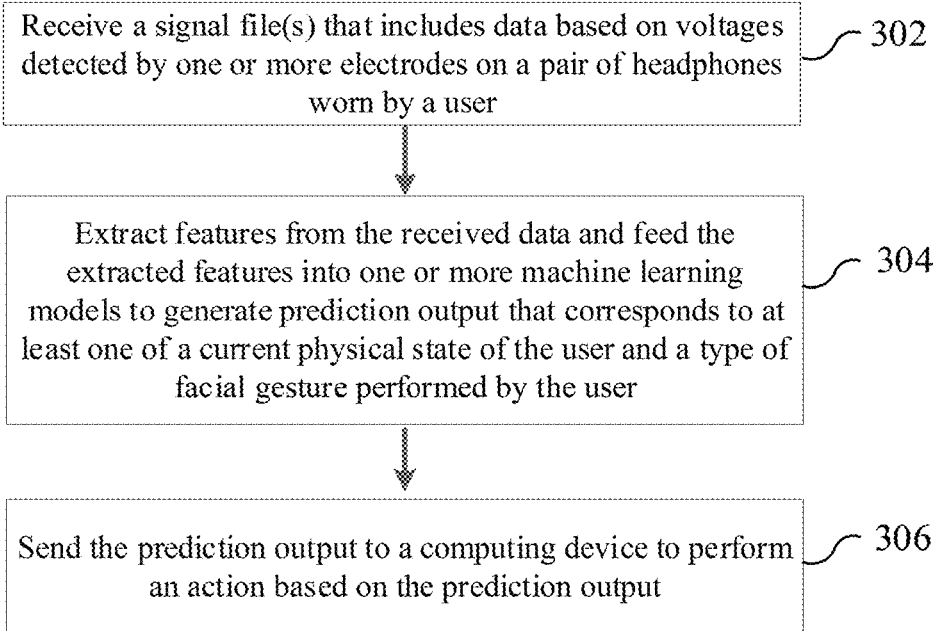

Receive a signal file(s) that includes data based on voltages detected by one or more electrodes on a pair of headphones worn by a user          302

Extract features from the received data and feed the extracted features into one or more machine learning models to generate prediction output that corresponds to at least one of a current physical state of the user and a type of facial gesture performed by the user          304

Send the prediction output to a computing device to perform an action based on the prediction output          306

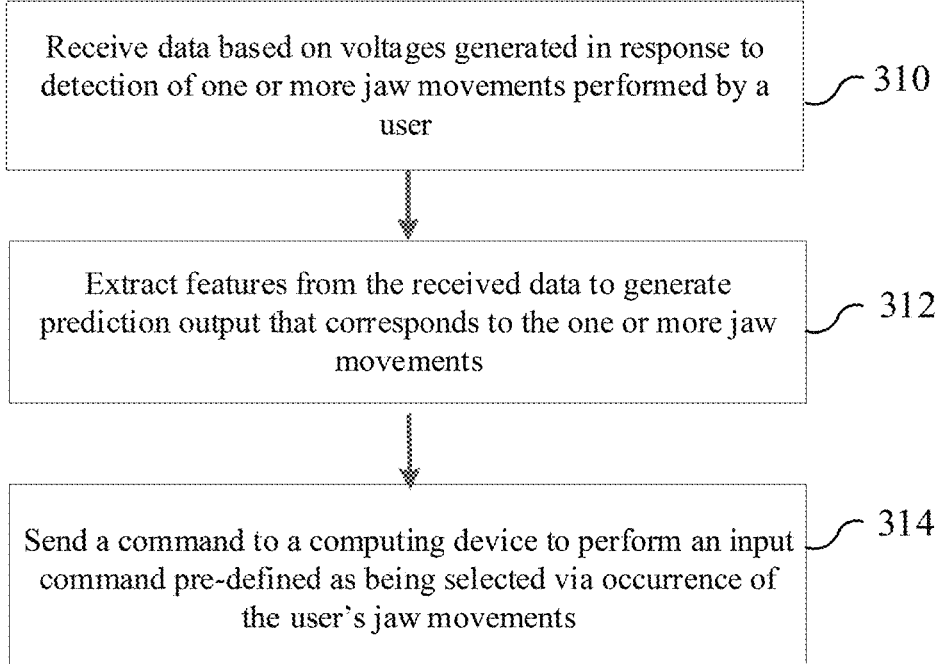

Receive data based on voltages generated in response to detection of one or more jaw movements performed by a user ⟋ 310

Extract features from the received data to generate prediction output that corresponds to the one or more jaw movements ⟋ 312

Send a command to a computing device to perform an input command pre-defined as being selected via occurrence of the user's jaw movements ⟋ 314

FIG. 3B

DETERMINING MENTAL STATES BASED ON BIOMETRIC DATA

CROSS-REFERENCE TO RELATED APPLICATIONS

This application is a continuation of U.S. patent application Ser. No. 17/122,085, filed on Dec. 15, 2020, which is hereby incorporated by reference in its entirety.

BACKGROUND

In the field of computer science, artificial intelligence ("AI.") networks, such as neural networks and deep learning networks, are increasingly being employed to solve a variety of tasks and challenging problems. Such A.I. networks can consist of layers of computational graphs with nodes representing computational operations and connections in between those operations and/or computational graphs with filters representing the extraction of features from input data. Each operation computes or extracts something from the input data and/or previous layer in order to produce output data and/or next layer. Within AI networks there are fairly predefined operations, and there can be, e.g., hundreds or thousands of these operations. Such operations can represent such computational tasks as matrix multiplication and convolution, often using many pieces of input data from within the network.

SUMMARY

Conventional systems lack the functionality for monitoring neural signals, brain signals, and muscle signals to infer a user's mental state and/or determine a selected input command, particularly in a manner that is comfortable and user-friendly in normal settings outside of a laboratory or research environment Various embodiments of an apparatus, methods, systems, and computer program products described herein are directed to the passive monitoring of biometric data and neural data via an Analytics Engine that receives data based on signals detected by a set of headphones worn by a user. Various types of signals may represent various types of facial movements or head movements performed by a user wearing the headphones and each respective facial or head movement may correspond to an input command for a computing device(s). Various types of signals may also represent various types of mental states or intensity level of various types of mental states.

According to various embodiments, the Analytics Engine receives data based on voltages detected by one or more electrodes on a set of headphones worn by a user. The Analytics Engine extracts features from the received data and feeds the extracted features into one or more machine learning models to generate a determined output that corresponds to at least one of a current mental state of the user and a type of facial gesture performed by the user. The Analytics Engine sends the determined output to a computing device to perform an action based on the determined output. For example, the Analytics Engine receives neural signals from the headphones worn by a user, that generates a determined output that corresponds to a specific jaw movement (e.g. a double jaw clench) based on the neural signals detected by the electrodes on headphones worn by a user when the user performed said jaw movement, and sends a command to a computing device associated with the user's headphones to perform an input command pre-defined as being selected via said jaw movement.

According to various embodiments, one or more electrodes detect electroencephalogram (EEG) signals, electromyography (EMG) signals, and/or Electrocardiogram (ECG) signals. Each of the electrodes on the set of headphones may be situated in or around the region of the headphones designed to make contact with the ear region of a user's head. For example, the electrodes may be situated on a respective ear cuff cushion of the set of headphones and engaged with conductive fabric of the ear cuff cushion, such that the electrodes make electrical contact with a user through the conductive fabric.

According to various embodiments, the Analytics Engine may be on a computing device that receives data from the set of headphones that it is associated with, for instance a user's cellphone or tablet or laptop. According to various embodiments, the Analytics Engine may be a cloud-based computing system that receives data from a computer device(s) that is associated with the set of headphones. According to various embodiments the Analytics Engine may be on a combination of a computing systems, for instance partially based on the user's headphones, partially based on the user's cellphone, and partially based in a cloud-based computing system. The Analytics Engine extracts EEG features from the received data that is based on EEG signals and extracts EMG features from the received data that is based on EMG signals. The Analytics Engine feeds the EEG features into various machine learning models to determine whether the user's current mental state represents any one or more of a degree or level of cognitive, emotional, or attentive states, for instance of focus, attention, distraction, cognitive load, fatigue, curiosity, certainty, doubt, mind wandering, sleepiness, admiration, adoration, aesthetic appreciation, amusement, anger, anxiety, awe, awkwardness, boredom, calmness, confusion, craving, disgust, empathic pain, entrancement, excitement, fear, horror, happiness, interest, joy, nostalgia, relief, romance, sadness, satisfaction, sexual desire, or surprise. For example, the Analytics Engine may report said level of focus back to the user. The Analytics Engine feeds the EMG features into a facial gesture machine learning model for determining a type of facial gesture from a plurality of types of facial gestures, for instance a jaw movement, a jaw clench, a tooth click, a smile, a blink, a wink, and/or a head movement, wherein different facial gestures are mapped to certain input commands.

According to various embodiments, the Analytics Engine may also receive data from a motion detector(s), such as one or more accelerometers (accel) and/or one or more gyroscopes (gyro) in the set of headphones to detect movement of the user's head while wearing the set of headphones. The Analytics Engine may also extract one or more movement features, such as accel features or gyro features based on the data it receives from the motion detector. The Analytics Engine feeds the accel features and/or gyro features and/or along with one or more of the EMG features into various machine learning models for determining a type of facial gesture and/or a type of head movement, wherein each is mapped to certain type(s) of interactions. For example, the facial and head gesture may include a combination, either simultaneously or sequentially, of a head nod and a blink, which may be mapped to a specific interaction. Each respective interaction(s) thereby corresponds to a type of input command(s) and/or a trigger to initiation one or more input commands at a computing device(s).

According to various embodiments, the Analytics Engine identifies an interaction that maps to the determined type of facial gesture in the determined output. A respective interaction comprises a type of user input represented by a respective facial gesture and/or head gesture for processing by the computing device associated with the set of headphones based on an occurrence of the respective facial gesture.

Further areas of applicability of the present disclosure will become apparent from the detailed description, the claims and the drawings. The detailed description and specific examples are intended for illustration only and are not intended to limit the scope of the disclosure.

BRIEF DESCRIPTION OF THE DRAWINGS

The present disclosure will become better understood from the detailed description and the drawings, wherein:

FIG. 3A is a diagram illustrating an exemplary method that may be performed in some embodiments.

FIG. 3B is a diagram illustrating an exemplary method that may be performed in some embodiments.

DETAILED DESCRIPTION

Figure 1A:
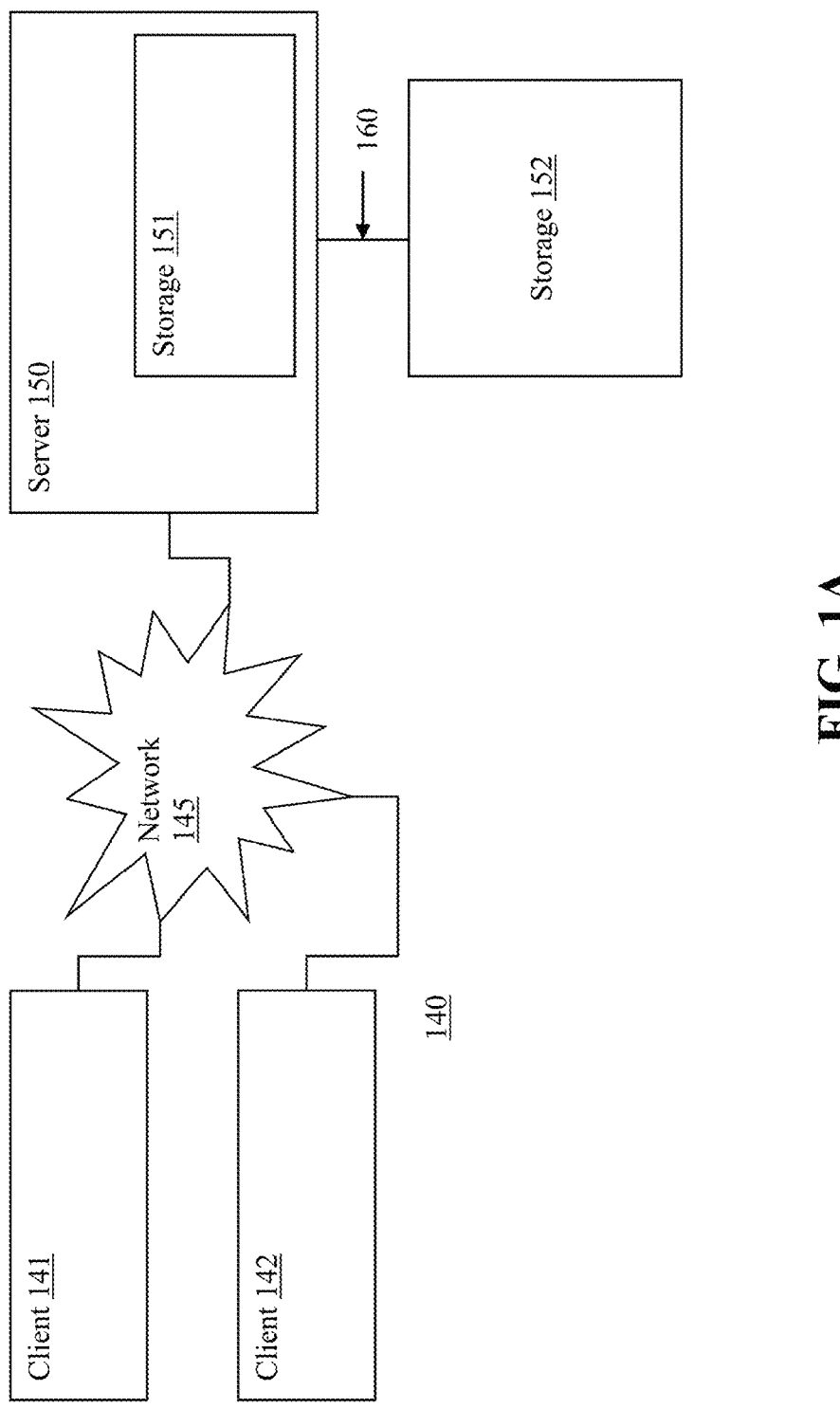
FIG. 1A is a diagram illustrating an exemplary environment in which some embodiments may operate.

In this specification, reference is made in detail to specific embodiments of the invention. Some of the embodiments or their aspects are illustrated in the drawings.

For clarity in explanation, the invention has been described with reference to specific embodiments, however it should be understood that the invention is not limited to the described embodiments. On the contrary, the invention covers alternatives, modifications, and equivalents as may be included within its scope as defined by any patent claims. The following embodiments of the invention are set forth without any loss of generality to, and without imposing limitations on, the claimed invention. In the following description, specific details are set forth in order to provide a thorough understanding of the present invention. The present invention may be practiced without some or all of these specific details. In addition, well known features may not have been described in detail to avoid unnecessarily obscuring the invention.

In addition, it should be understood that steps of the exemplary methods set forth in this exemplary patent can be performed in different orders than the order presented in this specification. Furthermore, some steps of the exemplary methods may be performed in parallel rather than being performed sequentially. Also, the steps of the exemplary methods may be performed in a network environment in which some steps are performed by different computers in the networked environment.

Some embodiments are implemented by a computer system. A computer system may include a processor, a memory, and a non-transitory computer-readable medium. The memory and non-transitory medium may store instructions for performing methods and steps described herein.

A diagram of exemplary network environment in which embodiments may operate is shown in FIG. 1A. In the exemplary environment 140, two clients 141, 142 are connected over a network 145 to a server 150 having local storage 151. Clients and servers in this environment may be computers. Server 150 may be configured to handle requests from clients.

The exemplary environment 140 is illustrated with only two clients and one server for simplicity, though in practice there may be more or fewer clients and servers. The computers have been termed clients and servers, though clients can also play the role of servers and servers can also play the role of clients. In some embodiments, the clients 141, 142 may communicate with each other as well as the servers. Also, the server 150 may communicate with other servers.

The network 145 may be, for example, local area network (LAN), wide area network (WAN), telephone networks, wireless networks, intranets, the Internet, or combinations of networks. The server 150 may be connected to storage 152 over a connection medium 160, which may be a bus, crossbar, network, or other interconnect. Storage 152 may be implemented as a network of multiple storage devices, though it is illustrated as a single entity. Storage 152 may be a file system, disk, database, or other storage.

In an embodiment, the client 141 may perform the method 200 or other method herein and, as a result, store a file in the storage 152. This may be accomplished via communication over the network 145 between the client 141 and server 150. For example, the client may communicate a request to the server 150 to store a file with a specified name in the storage 152. The server 150 may respond to the request and store the file with the specified name in the storage 152. The file to be saved may exist on the client 141 or may already exist in the server's local storage 151.

In another embodiment, the client 141 may be a set of headphones that sends biometric or motion sensor data used during execution of the method 200 or other method herein. This may be accomplished via communication over the network 145 between the client 141 and server 150. For example, the client may communicate a request to the server 150 to store a file with a specified file name in the storage 151. The server 150 may respond to the request and store the file with the specified name in the storage 151. The file to be saved may exist on the client 141 or may exist in other storage accessible via the network such as storage 152, or even in storage on the client 142 (e.g., in a peer-to-peer system).

In accordance with the above discussion, embodiments can be used to store a file on local storage such as a disk or on a removable medium like a flash drive, CD-R, or DVD-R. Furthermore, embodiments may be used to store a file on an external storage device connected to a computer over a connection medium such as a bus, crossbar, network, or other interconnect. In addition, embodiments can be used to store a file on a remote server or on a storage device accessible to the remote server.

Furthermore, cloud computing is another example where files are often stored on remote servers or remote storage systems. Cloud computing refers to pooled network resources that can be quickly provisioned so as to allow for easy scalability. Cloud computing can be used to provide software-as-a-service, platform-as-a-service, infrastructure-as-a-service, and similar features. In a cloud computing environment, a user may store a file in the "cloud," which means that the file is stored on a remote network resource though the actual hardware storing the file may be opaque to the user.

Figure 1B:
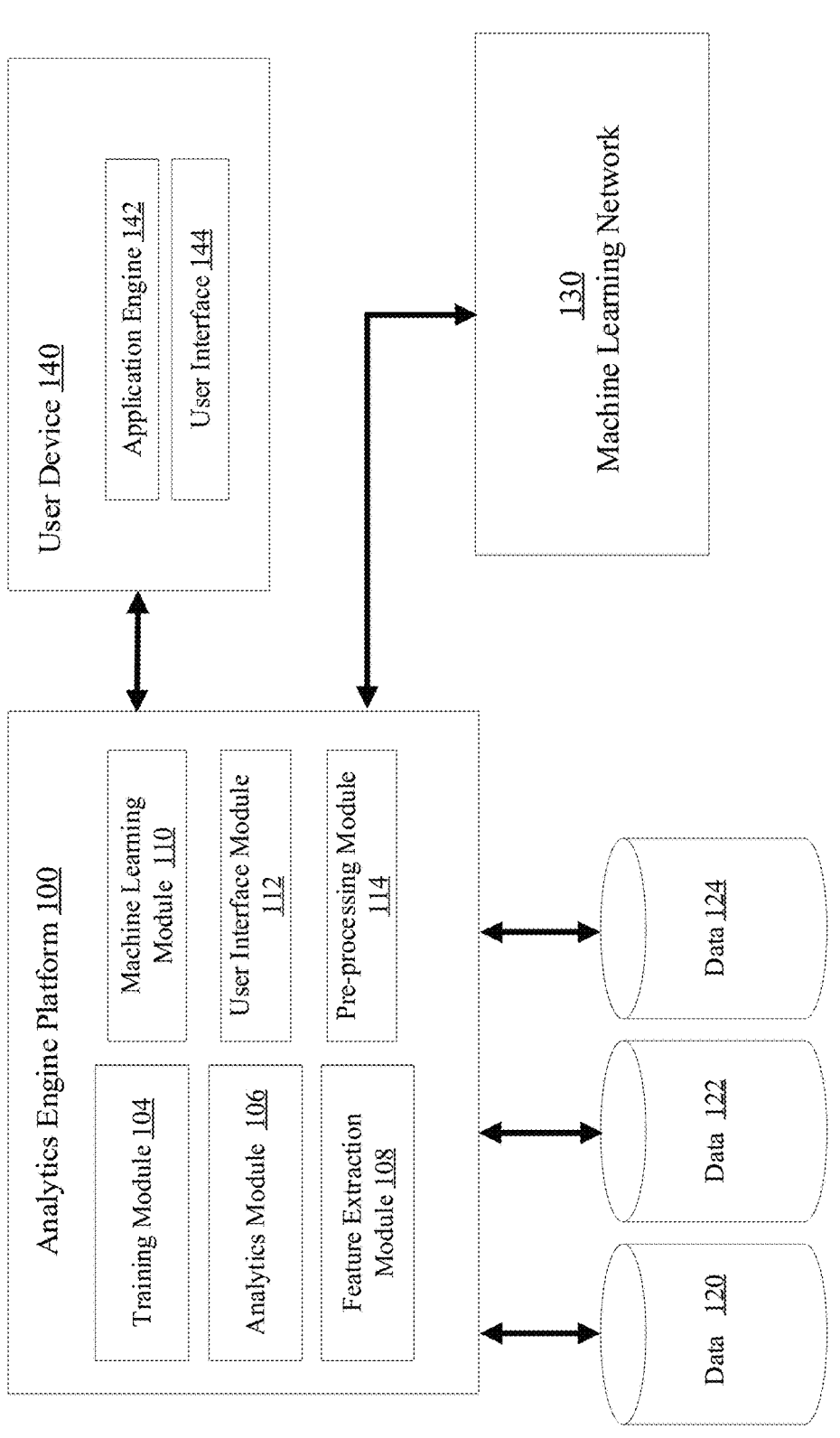
FIG. 1B is a diagram illustrating an exemplary environment in which some embodiments may operate.

FIG. 1B illustrates a block diagram of an example Analytics Engine Platform 100 for an that includes a training module 104, an analytics module 106, a feature extraction module 108, a machine learning module 110, a user interface (U.I.) module 112 and a pre-processing module 114. The platform 100 may communicate with a user device 140 to display output, via a user interface 144 generated by an application engine 142. The user device 140 may also communicate with the headphones 202.

The training module 104 of the system 100 may perform functionality as illustrated in FIGS. 2A, 2B, 2C, 2D, 2E 3A, 3B, 4, 5, 6A and 6B ("2A-6B").

The analytics module 106 of the system 100 may perform functionality illustrated in FIGS. 2A-6B.

The feature extraction module 108 of the system 100 may perform functionality illustrated in FIGS. 2A-6B.

The machine learning module 110 of the system 100 may perform functionality as illustrated in FIGS. 2A-6B.

The user interface module 112 of the system 100 may display information based on functionality as illustrated in FIGS. 2A-6B.

The pre-processing module 114 of the system 100 may perform functionality as illustrated in FIGS. 2A-6B.

While the databases 120, 122 and 124 are displayed separately, the databases and information maintained in a database may be combined together or further separated in a manner the promotes retrieval and storage efficiency and/or data security. In one or more embodiments, the Analytics Engine Platform 100 the machine learning network 130 and the data 120, 122, 124 may all be implemented within one or more computing devices.

In various embodiments, the Analytics Engine sends determined output for display in a user interface. For example, the user interface may display a visualization, such as a graph, of a user's change in, a degree, or a level of focus, attention, cognitive load, fatigue, curiosity, certainty, doubt, mind wandering, sleepiness, admiration, adoration, aesthetic appreciation, amusement, anger, anxiety, awe, awkwardness, boredom, calmness, confusion, craving, disgust, empathic pain, entrancement, excitement, fear, horror, happiness, interest, joy, nostalgia, relief, romance, sadness, satisfaction, sexual desire, and/or surprise at a specific point in time or over a particular period of time. Such data aggregation for visualization may be performed via the analytics module 106 and the output from the aggregation may be sent back to the computing device for display in a user interface. In various embodiments, a visualization may show a relationship between the mental state of the user and a particular activity, such as a graph of a user's change in focus with respect to the user listening to different genres of music, with respect to different time periods of the day, with respect to location (e.g. at home, in the office, or at the coffee shop), with respect to days of the week, with respect to a relationship to another event preceding the particular activity (e.g. after exercising), and/or combinations thereof. In various embodiments a visualization may display the graph of a particular mental state along with annotations about the user based on data from the headphones that the analytics module is able to learn from the headphones or in some cases other devices associated with the headphones. In various embodiments, the Analytics Engine Platform is able to determine if the user is performing a certain facial gesture (e.g. if the user is smiling) and the user's level of a certain mental state (e.g. happiness) can send the determined output for display in a user interface that displays a graph of the user's mental state, that is also annotated with specific times or moments when a user was smiling. In another example, the Analytics Engine Platform 100, may by monitoring the level of focus of a user, and may also be monitoring if the user is performing certain facial gestures, like a furrowing of the brow, that is associated with focus or concentration; the Analytics Module 106 may aggregate such data for visualization and may be displayed to the user, indicating that during periods of high focus or concentration rates of brow furrowing increased. Particularly when certain facial gestures are associated with particular mental states these types of features can be especially useful (e.g. smiling/happiness, head-tilt/questioning, lowering-of-the-head/sadness, eyes-wide-open-unblinking/attention, raising-of-eyebrows/surprise, lifting-of-lip/disgust) The Analytics Engine may determine when a notification should be sent to a user's computing device in anticipation or upon detection of a change in the user's mental state. For example, a notification may indicate to the user that the user is entering a time of day during which the user tends to lose focus, gain focus, experience more/less fatigue or more/less sleepiness. For example, a notification may indicate to the user that their focus level has recently dropped and their mental fatigue level has increased, and suggest to the user to take a break or perform a physical activity (e.g. standing up, stretching, walking, exercising, doing yoga, doing calisthenics, and/or simply actively resting)

Figure 2A:
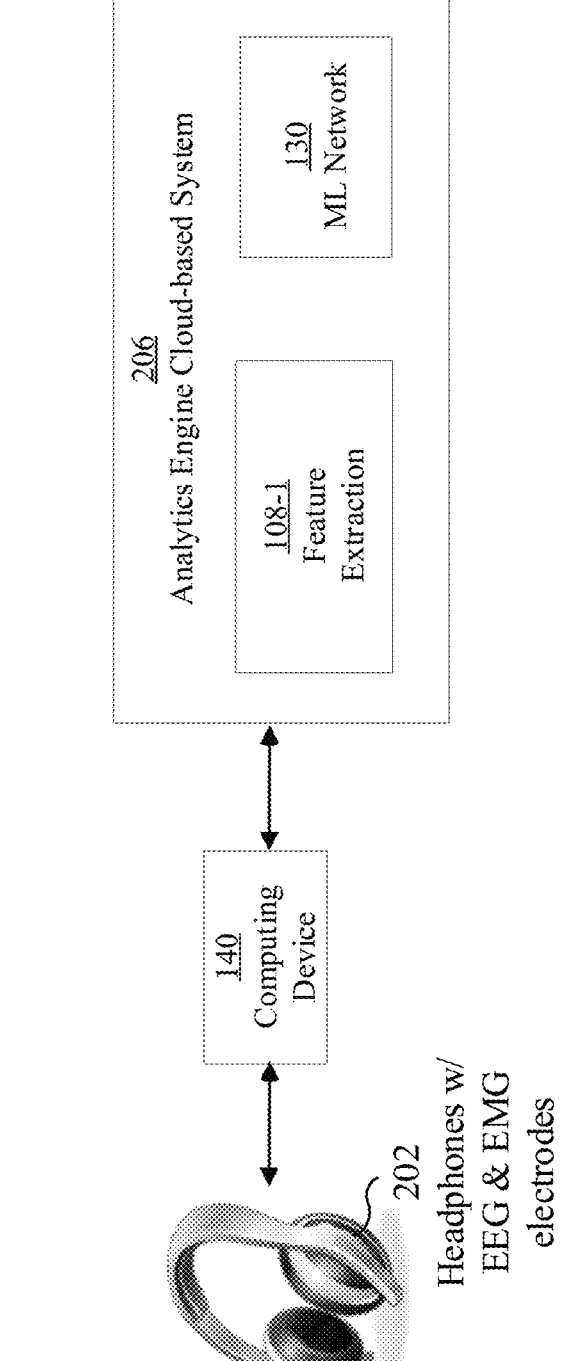
FIGS. 2A, 2B, 2C, 2D and 2E are each a diagram illustrating an exemplary environment in which some embodiments may operate.

As shown in diagram 200 of FIG. 2A, one or more embodiments of the Analytics Manager may include a system that includes a set of headphones 202 whereby a user wearing the headphones 202 can interact with (or control) a computer device(s) 140 based on data from electrodes on the headphones 202. The electrodes continually monitor and detect voltages and the signals are sampled, digitized (e.g. using an a/d converter), and converted to a floating-point representation of time series data that are buffered on the headphones 202. The time series data is aggregated, then packaged into a network compatible format for sending to an associated device (e.g. sending via Bluetooth to a connected smartphone). In various embodiments the data may be further sent from the associated device (e.g. a smartphone) to the cloud, for instance using Kafka over a secure socket connection (SSL) for storage and/or analysis. The user may perform one or more facial gestures that may be detected by the one or more electrodes integrated into the headphones. A facial gesture may be, for example, a jaw movement, a jaw clench, a jaw wiggle left and right, a jaw jutting (e.g. jutting jaw forward and backward), a jaw opening, a tooth click, a smile, a cheek puff, a cheek suck, a blink, a wink, a tongue movement, a nose movement, an inhalation or exhalation, an eye movement, a frown, an eyebrow raise, an eyebrow lowering, a mouth movement, a whispered word or phrase, a silent vocalization, and any type of facial muscle movement, head movement, and any type of jaw movement, asymmetric variations of the former, and combinations thereof. For instance, a facial gesture may include a double jaw clench (consisting of two consecutive jaw clenches in a short time window), or a left-right-left-right jaw wiggle (consisting of a jaw moving first left, then right, then left, then right in a short time window). For instance, the user may wink with just the left eye or just the right eye, or the user may puff out just the left cheek or just the right cheek. The facial gesture may also include certain types of gestures that are very subtle, for instance the action of silently vocalizing a word. In certain scenarios a user may not want their facial gestures to be noticed by others, or may not want certain commands to be heard by others. In this case one can silently move their mouth as if they were stating a specific word, but not actually saying it out loud. By moving their mouth as if they were saying the word, the muscles in the mouth, tongue, neck, face, and lips move, and the movement of those muscles can be detected by the sensors on the headphones. In various embodiments, this type of silent vocalization (SiVox) can be detected by the one or more electrodes integrated into the headphones. one Data from the electrodes may represent the detected facial gestures that correspond to a defined interaction. In various embodiments, the voltages may be generated by neurons in the user, and/or as a result of muscle movements and/or from brain waves and/or from other neural signals. A defined interaction may be mapped to a type of action. The system may implement the mapped action based on appropriate electrode data. In various embodiments a user interface may present the user with options to map/establish certain actions that are associated with specific facial gestures. For instance, a user may be presented with a list of facial gesture inter-actions and the user may then select certain actions to be associated with each interaction, like a double-jaw-clench-→may be mapped to a mouse click, a head-nod-with-a-blink→may be mapped to a play/pause function in an audio/video application, a double-eyebrow-raise→may be mapped to opening a new file or application. A user may be presented the option to create new combinations of gestures and map them to different actions or combinations of actions. In various embodiments, a user interface may present the user with options to set certain thresholds for certain levels of mental states, along with actions to perform if the threshold is met or exceeded. For example, the analytics engine may determine if a user's level of focus has exceeded a certain threshold set by the user in the user interface, and if the user's level of focus has exceeded that threshold, then the Application Engine my send instructions to the User Device to disable notifications (e.g. enter a Do Not Disturb mode) that may be distracting to the User, thereby assisting the user to maintain a high level of focus.

In various embodiments, the headphones have a visual indicator (e.g. a light) that corresponds to different mental states (e.g. different colors), to levels of mental state (e.g. brightness light), and/or to certain thresholds of levels of mental states (e.g. on/off). For example, the visual indicator could serve as a type of 'mood ring', that changes color based on the mental state of the user. For example, the visual indicator could serve as a visual notice of the user being above a certain threshold of focus, so that a visual indicator on the headphones turns red to indicate that the user should not be disturbed, or if the user is below a certain threshold of focus the light turns green. In various embodiments, if a user is above a certain threshold of a mental state, and/or above a certain level of a mental state for a certain level of time, there is also a haptic feedback indicator (e.g. a vibrate sensation), that alerts the user of a notification. In various embodiments, the visual indicator is used as a driver of social interaction. For instance, if a user is above a certain threshold of mental fatigue, or has been above a certain level of mental fatigue for a certain level of time, then a haptic notification may be sent to the user (e.g. the headphones vibrate according to a certain pattern), a notification may be sent to the user's computing device to indicate that the user should take a break (e.g. a notification on the user's smartphone prompting the user to take a break), and/or a visual indicator on the headphones might light-up or change color (e.g. from do-not-disturb red when the user was focused, to needs-a-break blue when the user is mentally fatigued), which indicates to others around the user that the user is mentally fatigued and needs to take a break so the others know they can, and perhaps should interrupt the user to go on a walk together In various embodiments, if a user is above a certain threshold of a mental state, and/or above a certain level of a mental state for a certain level of time, there is also a haptic feedback indicator (e.g. a vibrate sensation), that alerts the user of a notification.

In various embodiments, the headphones also contain an accelerometer and/or a gyroscope which provide movement data to the computing device. The movement data can be combined with the EMG data to determine certain types of head movements, or head movements combined with facial gestures. Head movements may include head tilts, head nods, head shakes, head rotations, or the like, and may be combined with the facial gestures discussed above sequen-tially or coincidentally to indicate a certain desired interac-tion. A defined combination or sequence of interactions may be mapped to a type of action.

The headphones 202 perform pre-processing and data is sent to the computer device(s) 140 and/or then to a cloud computing environment 206 for feature extraction 208 and feeding extracted features into a machine learning network 130. Output from the machine learning network 130 may be sent to the computing device 140 and may represent one or more types of actions to be performed or executed. Output from the machine learning network 130 may be sent to the headphones 202 via the computer device(s) 140 and/or a cloud computing environment 206. Output may represent one or more types of actions to be performed.

According to various embodiments, the buffered data on the headphones 202 is converted into network packets, which are transmitted from the headphones 202 to the computing device(s) 140. In some embodiments the com-puting device 140 has a self-contained analytics engine platform 100. The computing device 140 relays the one or more portions of the buffered data to the cloud computing platform 206. The cloud computing platform 206 performs preprocessing, and signal processing, and analysis, and machine learning techniques to generate output. The output is sent back from the cloud computing platform 206 to the computing device(s) 140. The computing device(s) 140 perform one or more actions based on the received output. In various embodiments, the computing device 140 that sends the buffered data to the cloud computing platform 206 may be different than a device that performs the one or more actions based on the received output sent back from the cloud computing platform 206. In some embodiments the headphones have a self-contained computing device built into the hardware of the headphones. In some embodiments different parts and/or all of the preprocessing, signal pro-cessings, analysis, and machine learning processes can be executed on one or more computing devices and/or cloud computing platforms.

According to various embodiments, the headphones 202 may be at least one of: circum-aural headphones, supra-aural headphones, headband headphones, over the ear head-phones, earbud headphones, earpiece headphones, and bone conduction headphones.

Figure 2B:
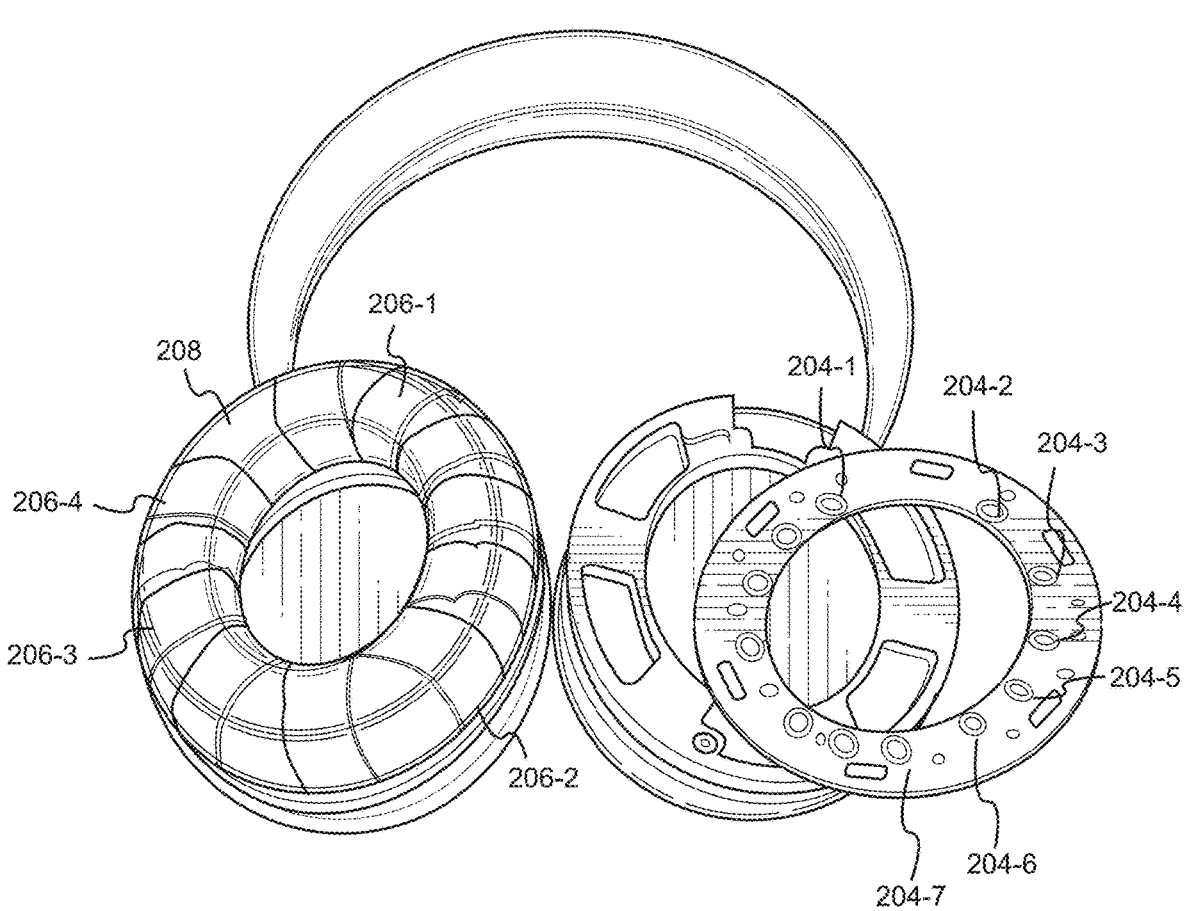

According to various embodiments, as shown in FIG. 2B, the headphones 202 may be (or include) a neural recording device configured to capture, record and/or transmit neural control signals from one or more brain regions indicating activity in the brain regions. The neural recording device can include any suitable recording device or system configured to record neural activity between the neurons, using any suitable approach. The neural recording device includes one or more electrodes 204-1, 204-2, 204-3, 204-4, 204-5, 204-6, 204-7 that are configured to capture and record the neural signals from the one or more brain regions or one or more muscles. It is understood that a subset of the electrodes 204-1, 204-2, 204-3, 204-4, 204-5, 204-6, 204-7 illustrated in FIG. 2B are accompanied by a corresponding reference numeral. It is further understood that one or more features illustrated in FIG. 2B that are similar in appearance to electrodes 204-1, 204-2, 204-3, 204-4, 204-5, 204-6, 204-7 may also be interpreted as representing one or more additional electrodes. In some embodiments, the neural recording device can be configured to record and neural signals including signals that represent a user's voluntary muscle movements (e.g., eye-movements, postural movements, gestures) that can be used to implement a pointing control feature. In some embodiments the headphones may be configured to record involuntary muscle movements as well. In some embodiments, the signals acquired by the neural recording device can include neural signals corresponding to brain states such as cognitive, emotional, or attentive states of the user. In some embodiments, neural recording device can be configured to capture neural signals directly by electrically recording the primary ionic currents generated by neurons, the ionic currents flowing within and across neuronal assemblies. In some embodiments, neural recording device can be configured to capture neural signals indirectly by recording secondary currents or other changes in the nervous system, associated with or resulting from the primary currents. In some embodiments, the neural recording device can be specifically adapted to record one or more signals including a variety of signature brain signals such as Event Related Potentials (ERPs), Evoked Potentials ("Eps", e.g., sensory evoked potentials such as visually evoked potentials (VEP), auditory evoked potentials (AEP), motor evoked potentials), motor imagery, brain state dependent signals, slow cortical potentials, and other, as yet undiscovered, signature activity potentials underlying various cognitive, attentive or sensorimotor tasks. In some embodiments, the neural recording device can be specifically adapted to record one or more signals in the frequency domain. Some examples among others include sensorimotor rhythms, Event Related Spectral Perturbations (ERSPs), specific signal frequency bands like Theta, Gamma or Mu rhythms, etc. As described herein, the neural recording device can record neural activity signals to gather information related to cognitive processes of a subject (such as a user) through a recording stage that measures brain activity and transduces the information into tractable electrical signals that can be converted into data that can be analyzed by a processor(s). As described above, the neural recording device can include a set of electrodes 204-1 . . . 204-7 . . . that acquire electroencephalography signals from different brain areas. These electrodes can measure electrical signals caused by the flow of electric currents during synaptic excitations of the dendrites in the neurons thereby relaying the effects of secondary currents. The neural signals can be recorded through the electrodes in the neural recording device appropriately arranged around the ear and jaw of a user. As described above, the neural recording device can include a set of electrodes 204-1 . . . 204-7 . . . that acquire electromyography signals from different muscles, and that acquire electrocardiography signals from the heart.

One or more embodiments may include a set of headphones 202 with electrodes integrated with a conductive fabric 206-1, 206-2, 206-3, 206-4 (or one or more portions/strips of conductive fabric) of a headphone cushion 208. In some embodiments, the electrode may sit behind the conductive fabric integrated into a headphone ear cushion or ear pad. In some embodiments, on or in the ear cushion there are conductive strips of fabric 206-1, . . . 206-4 connected to non-conductive portions of the ear cushion 208 such that each conductive strip of fabric is not touching another adjacent conductive strip of fabric, and so that each conductive strip of fabric is electrically insulated from each other, and each strip of conductive fabric is connected to a distinct respective electrode such that the signal from each respective electrode can be distinguished from a neighboring electrode because the electrodes remain electrically insulated from each other. In some embodiments an electrode may be electrically connected to the conductive fabric such that the EEG, EMG, and/or other signals may be detected by the electrode through contact between the user's skin and the conductive fabric. In various embodiments, the electrodes are integrated behind the ear cushion on the headphones, and each of the respective electrodes are each in electrical contact with the each of the respective conductive fabrics of the ear cushion. In various embodiments, the electrodes are integrated into the ear cushion of the headphones, with the respective electrodes electrically in-contact with the respective islands (e.g. islands because the conductive fabric portions are electrical 'islands,' and not electrically in contact with neighboring conductive fabric portions, only electrically in contact with the sensor electrode) of conductive textile integrated into the outer material of the ear cup or ear cushion of the head phones that are positioned such that the conductive textile would make contact with the user's skin when wearing the headphones. It is understood that the conductive fabric could be a conductive textile, a conductive cloth, a conductive textile, a conductive yarn, a conductive fiber, a conductive foam, a conductive membrane, a conductive flexible conformal material, a conductive polymer, and/or a conductive polymer coated fabric and/or combinations thereof. In some embodiments the ear cushion of the headphones is made out of a rubberized type material, like silicone or thermoplastic urethane (TPU), in which case the electrodes may make contact with the user's skin through conductive polymer, or conductive wires or fibers that are integrated into the silicone or TPU material or other type of flexible conductive conformal material. It is understood that the electrodes can be integrated into the ear cup, ear cushion, Ear-Pads, earpads, ear-canal-probe, ear-bud, or other part of the headphones that make contact with a user's skin in or around the user's ear. In various embodiments, between the conductive fabric electrodes of the earcup 206-1, 206-2, . . . . 206-4, there are non-conductive portions of the earcup 208. The non-conductive portions of the earcup 208 spaced in-between each conductive portion of the earcup 206-1 . . . . 206-4, help ensure that each respective electrode remains electrically isolated from its neighboring electrode. According to one embodiment, one or more electrodes are placed at a location on the headphones 202 that results in a proximate alignment of the one or more electrodes with a location at which the user's jawbone is substantially close to the user's ear when the user wears the headphones 202. Another placement of one or more electrodes on the headphones 202 may result in a proximate alignment of the one or more electrodes with an area directly behind the user's ear when the user wears the headphones 202. Another placement of one or more electrodes on the headphones 202 may result in an approximate alignment with the user's temple. Another placement of one or more electrodes on the headphones 202 may result in an approximate alignment with the user's mastoid. Another placement of one or more electrodes on the headphones 202 may result in an approximate alignment of the electrodes with the user's temporomandibular joint area. According to various embodiments, all the electrode sensors 204-1 . . . 204-7 . . . on the headphones 202 may be situated behind a conductive fabric 206-1, 206-2, 206-3, 206-4 that covers one or more portions of a respective the ear cuff cushion(s) 208 and are electrically connected to the respective conductive portions of the ear cuff cushions. According to various embodiments, an electrode(s) may span at least 10%, at least 20%, at least 30%, at least 40%, at least 50%, at least 60%, at least 70%, at least 80%, at least 90%, at least 100%, or more of the width of the ear cuff cushion 208.

It is understood that a subset of the conductive fabric 206-1, 206-2, 206-3, 206-4 illustrated in FIG. 2B are accompanied by a corresponding reference numeral. It is further understood that one or more features illustrated in FIG. 2B that are similar in appearance to the conductive fabric 206-1, 206-2, 206-3, 206-4 may also be interpreted as representing additional conductive fabric (or additional portions of conductive fabric). It is understood that the electrode sensors 204-1, . . . 204-7 could be distinct from the conductive fabric and made to be in electrical contact. In other embodiments the electrode sensors 204-1, . . . 204-7 could be seamlessly integrated with the conductive fabric portions 206-1, . . . 206-4.

Figure 2C:
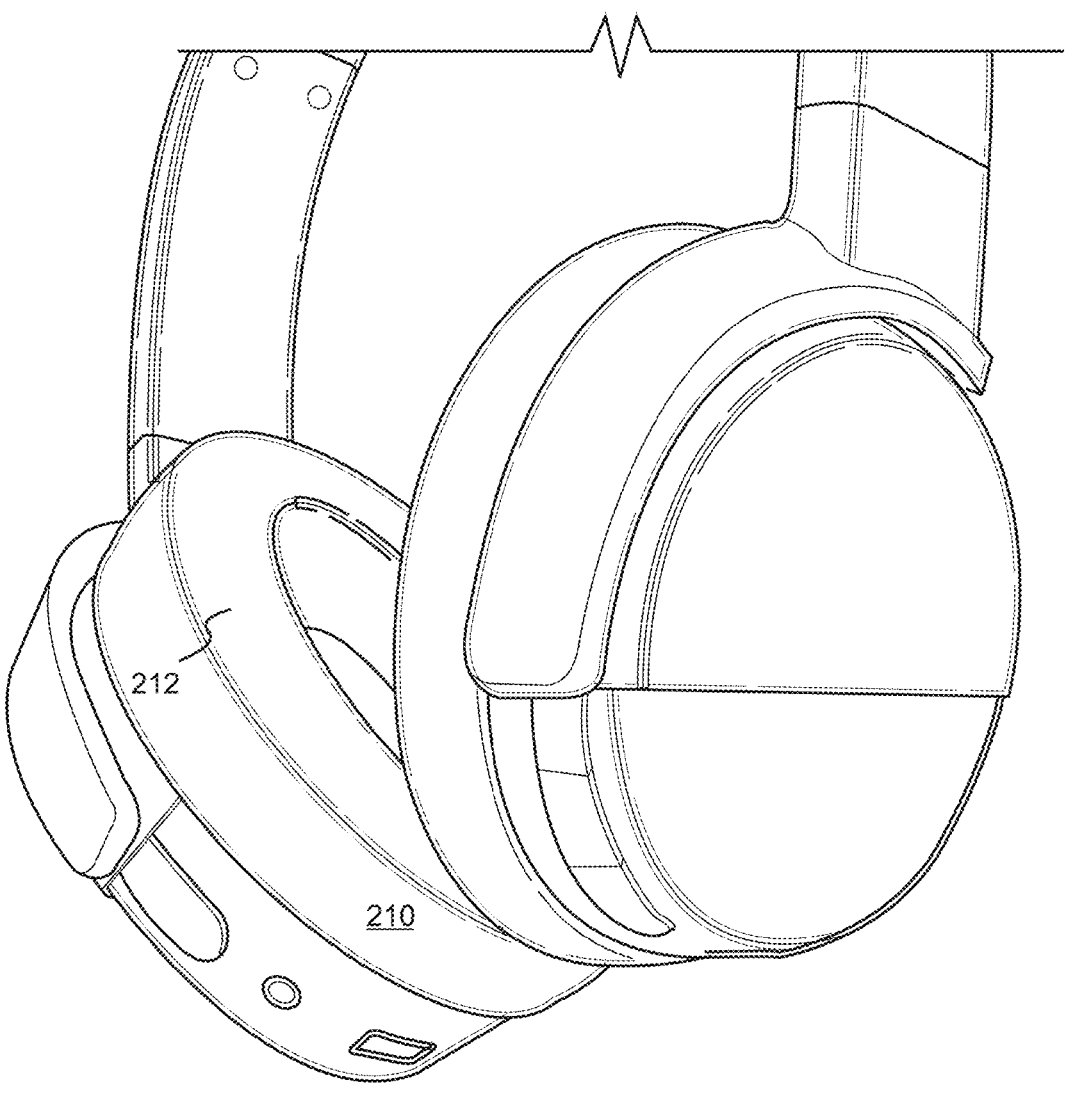
Figure 2D:
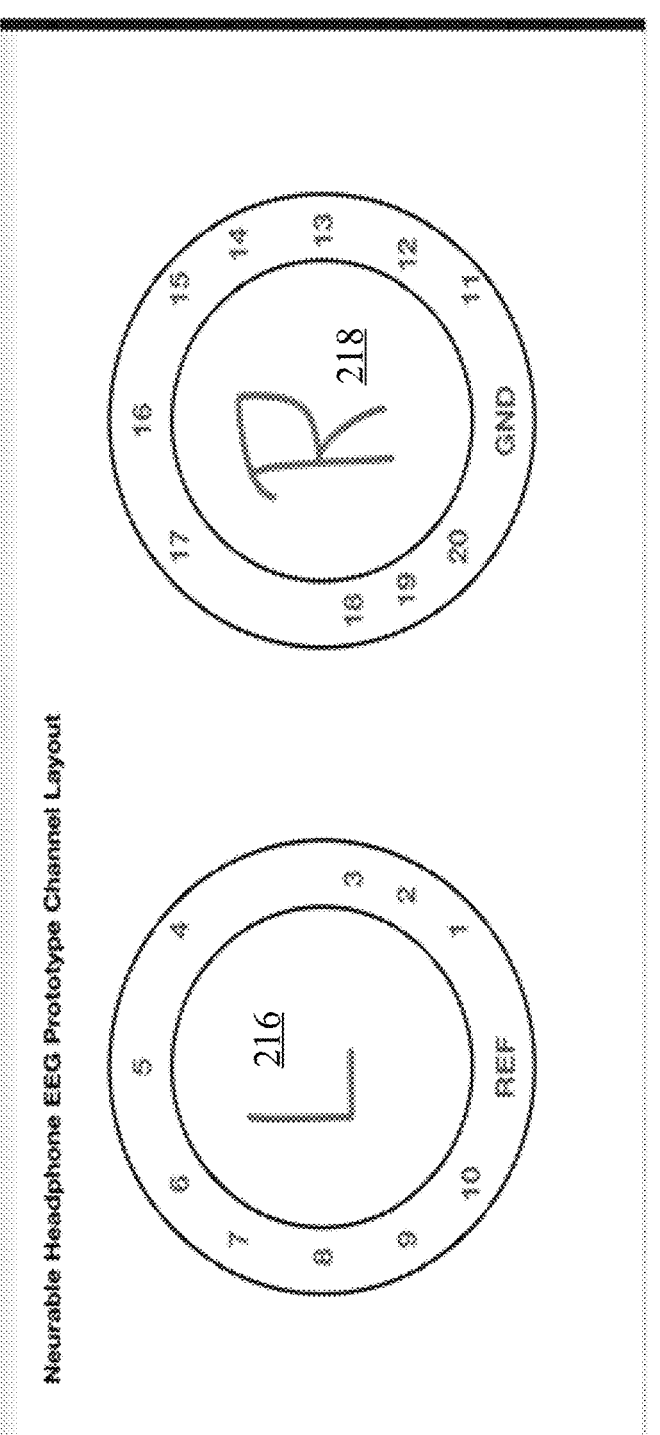
Figure 2E:
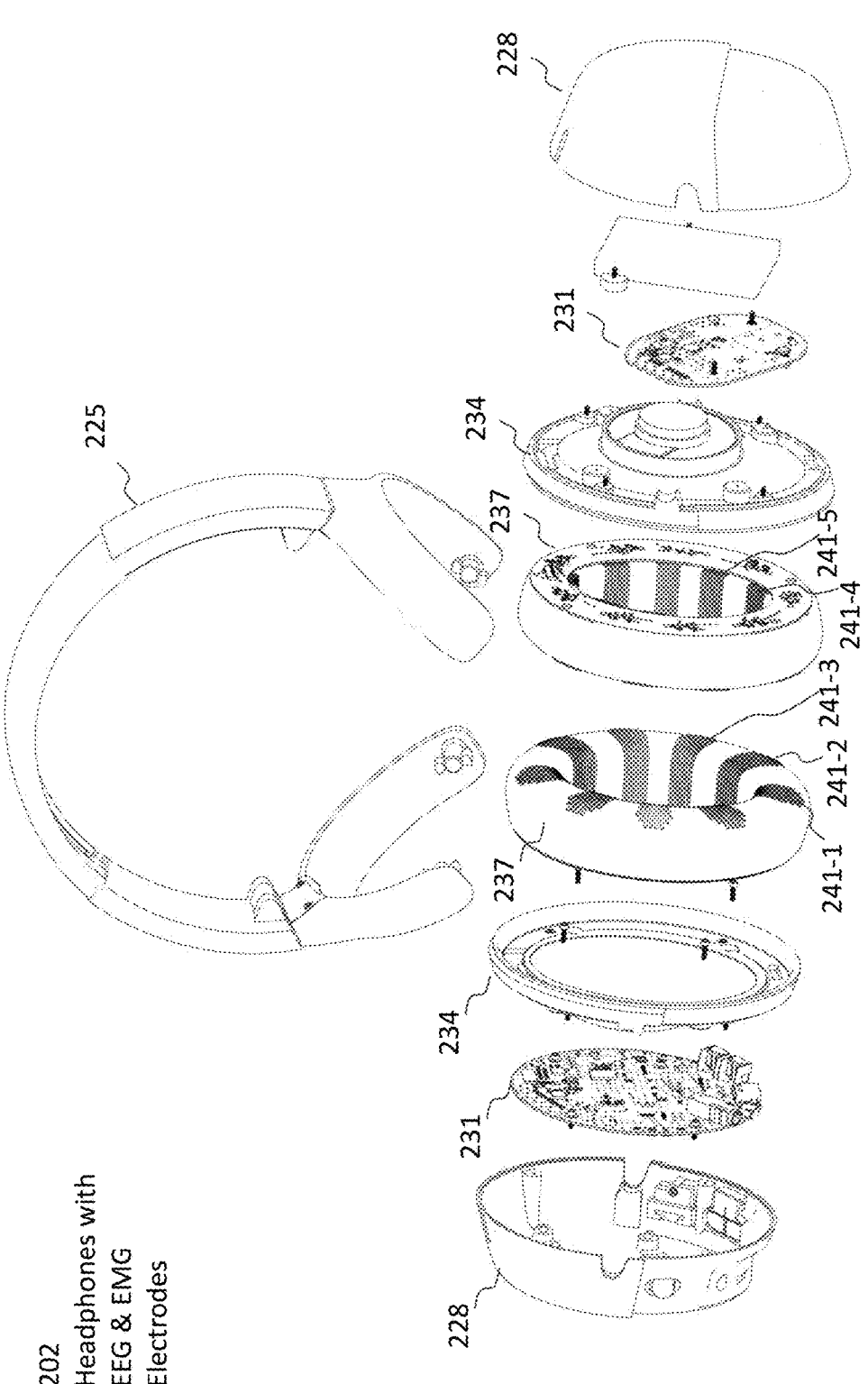

One or more embodiments is shown in FIG. 2E, showing 202 Headphones with EEG and EMG Electrodes integrated into the ear cushion. The headband of the headphones 225, connects to the case of the headphones 228. The headphones may contain a circuit board 231, which may include associated ports (e.g. charging port), input/output ports or antennae (e.g. 3.5 mm audio port, microphone, or Bluetooth antennae, WiFi antennae) and user interface/control buttons (e.g. volume button, play/pause button) that align and connect properly with the case 228, along with typical circuit board architectures like memory, and processors. The headphones may also contain speaker 234 or system that emits sound. The headphones may also contain the ear cushion 237 with integrated electrodes 241-1, 241-2, 241-3, 241-4, 241.5. It is understood that a subset of the conductive fabric electrodes integrated into the ear cushion 241-1, 241-2, 241-3, 241-4, and 241-5 illustrated in FIG. 2D are accompanied by a corresponding reference numeral. It is further understood that one or more features illustrated in FIG. 2E that are similar in appearance to conductive fabric electrodes integrated into the ear cushion 241-1, 241-2, 241-3, 241-4, and 241-5 may also be interpreted as representing additional conductive fabric electrodes integrated into the ear cushion.

As shown in FIG. 2C, a non-conductive textile covering 210 may be a top layer portion of an ear cuff cushion. A portion of the non-conductive textile covering 210, may be conductive fabric 212 that may further be integrated into the textile covering 210, whereby the portion of the conductive fabric 212 aligns with a respective electrode underneath or inside the ear cushion. As shown in FIG. 2.C, the textile covering 210 is a non-conductive fabric or material, with conductive fabric/materials 212 integrated therein. In various embodiments conductive fibers or materials are integrated into the ear cuff cushion through weaving, sewing, stitching, gluing, extruding, snapping, sliding, clasping, buttons, fasteners, grommets, eyelets, or any number of other methods.

It is understood that while conventional systems rely on electrodes placed at various locations on the top of a person's head, various embodiments described herein provide for the generation and output of meaningful data by electrodes placed solely near, in, and/or around a person's ears, such as substantially near a mastoid area, the occipital area behind the ear, the zygomatic region near the ear, the temporal region, the parotid-masseteric region, the auricular region, the temporomandibular joint area, the temple area, the sphenoid area, in the ear canal, and/or any defined facial region or head region in or around the ear, especially those areas that may be normally touched by a pair of headphones. While having additional electrodes in other areas of the face like the oral region or mental region, or parietal region or occipital region may be helpful for additional data for analysis, placing electrodes in those areas may be uncomfortable for users, and inhibit wearing or using of such devices, are visually unappealing, and may have social/societal issues using such devices in public. In various embodiments, the electrodes are integrated into the headphones in such a way as to be nearly invisible to an outside observer who will see 'normal-looking' headphones, and are integrated into headphones in such a way as to be comfortable for long-term wear, allowing a user to comfortably use the headphones for many hours continuously without needing or wanting to take them off. As shown in FIG. 2D, a diagram 214 includes a left ear headphone diagram 216 with one or more electrode locations 1, 2, 3, 4, 5, 6, 7, 8, 9 and 10. The diagram 214 further includes a right ear headphone diagram 218 with one or more electrode locations 11, 12, 13, 14, 15, 16, 17, 18, 19 and 20. Electrode location 1, 2, 3 and 18, 19, 20 are situated such that corresponding electrodes will be in substantial alignment near a mastoid area behind the right and left ear of a user when the user wears the headphones.

The headphones 202 may include one or more electrodes that can detect various types of signals, such as EEG and/or EMG signals. For example, one or more electrodes may detect EEG signals. In addition, one or more electrodes may detect EMG signals representing a movement of a user's facial muscle(s) when the user wears the set of headphones. In various embodiments the same electrode may be able to detect EEG, EMG, and ECG signals. In various embodiments the user can use certain facial gestures to interact with a computing device. For example, detection of one or more detected facial muscle movements and/or detected audible clicks caused by teeth movement and/or contact between various teeth may be mapped to an "interaction(s)." An interaction(s) may be processed as representative of a unit(s) and/or occurrence of user input whereby detected movements may be used to control a computing device(s) or define input for the computing device. For example, an interaction(s) may be defined as being mapped to a certain type and/or pattern of facial muscle movement(s) and correspond to one or more input commands to trigger one or more computing device actions.

According to various embodiments, an interaction(s) may emulate a user action applied to a peripheral input device (e.g. a mouse click). For a certain facial gesture(s), such as a smile for example, a preceding interaction may be defined as being required to occur prior to the smile within a duration of time. As such, the preceding interaction may emulate a request for a wake command in which a computing device is instructed to expect to receive a subsequent command. By implementing the requirement of the preceding wake request interaction before the occurrence of a smile, various embodiments may discern whether a smile is a coincidental physical action or a gesture performed by the user that is mapped to an wake request interaction intended to emulate input for the computing device.

According to various embodiments, a detected interaction(s) may be based on the occurrence and/or a sound of a sequence of teeth clicks (such as a double tooth click). For example, a sequence of teeth clicks may be mapped to represent a wake request interaction, which may be followed by a smile. The wake request interaction thereby corresponds to a wake command to trigger the computing device to monitor for an occurrence of at least one subsequent input for a defined period of time. Because the wake command alerts the computing device to expect a subsequent command, the detected smile will be determined to be an interaction that maps to a subsequent input command, rather than a coincidence.

Similarly certain facial gestures like a jaw clench may be difficult to for the Analytics Engine to distinguish if the user is intending to perform an interaction based on the jaw-clench interaction or if the user is simply chewing. To address this issue, according to various embodiments, a sleep request interaction may correspond to a sleep command to trigger the computing device to ignore subsequent detected facial gestures. For example, a detected interaction based on a head-nod-simultaneous-to-a-blink may represent a sleep command, which may be followed by chewing. Because the sleep command alerted the computing device to ignore subsequent facial gestures, the device may ignore the user's subsequent chewing rather than trying to determine if the user is attempting to perform an interaction. For example, a detected interaction based on a pre-defined type or pattern of jaw movement may represent a type of command and/or user input.

As shown in the flowchart 300 of FIG. 3A, the Analytics Engine receives one or more signal files that include data based on voltages detected by one or more electrodes on a set of headphones worn by a user (Act 302). According to various embodiments, an electrode(s) for detecting EEG signals makes electrical contact with the user's skin with respect to a mastoid area of the user and an electrode(s) for detecting EMG signals makes electrical contact with the user's skin with respect to a temporomandibular joint area of the user, and another electrode(s) for detecting EEG signals makes electrical contact with the user's skin with respect to a temple area of the user, and another electrode(s) makes electrical contact with the user's skin with respect to the auricular region of the user. The signal files may further include audio data and movement data, from which audio and movement features may be extracted. For example, the signal files may include audio data based on sound detected by one or more microphones associated with at least one of the electrodes. The signal files may further include movement data based on at least one change in a physical orientation of a motion detector associated with the set of headphones. In various embodiments the audio signal may be associated with a facial gesture, for instance a clicking of the teeth creates an audible "click" sound but also uses muscles to move the jaw and thereby creates EMG signals that can be picked up by the electrodes. In this embodiment, the audio signal may be detected by one or more microphones, converted from analog audio signal to a digital signal, and sent to the analytics engine platform 100 wherein the Feature Extraction Module 108 may extract audio features and send those features to the Machine Learning Network 130 along with the extracted EMG features associated with the facial gesture. In other various embodiments the facial gesture may include a very softly whispered word, which may be whispered too softly for another person to hear (e.g. a non-audible murmur or NAM) and maybe so softly that there is no or limited vibrations of the user's vocal folds, but wherein the microphones are able to pick-up certain vibrations traveling through the user's skin/tissue/ bone, especially is the microphone is a very sensitive microphone or a NAM microphone specifically (e.g. that operate similar to a stethoscope). In this embodiment, when a user softly whispers a word, the audio/vibration data from the microphone is sent to the Analytics Engine Platform along with the EMG data, the Feature Extraction Module extracts NAM features and EMG features, and those features are sent to the Machine Learning Module 110, to determine what word was whispered, the determined output. In this embodiment, the combination and NAM features and EMG features allows the system to better determine what word(s) were whispered. Further, natural language processing (NLP) may be used, to help determine what word(s) were spoken, their meaning/intent, and the determine output may be sent to a computing device to perform an action based on the determined output. In this embodiment because the microphone may be picking up vibrations in the user's tissues generated by a non-audible whisper, along with EMG signals, the system may be more robust an determining the user's intended interaction (e.g. a whispered command, or a whispered dictation) than a standard speech-recognition-microphone system especially in noisy environments.

The Analytics Engine extracts features from the received data and feeds the extracted features into one or more machine learning models to generate determined output that corresponds to a current mental state of the user and a type of facial gesture performed by the user (Act 304). The Analytics Engine extracts EEG features from the received data based on EEG signals detected by the one or more electrodes and feeds the extracted EEG features into one or more differing machine learning models, whereby the machine learning models predict the user's current level of focus, fatigue, and/or sleepiness and/or any number of other mental, cognitive, or attentive states. The Analytics Engine extracts EMG features from the received data based on EMG signals detected by the one or more electrodes. The Analytics Engine feeds the extracted EMG features into a facial gesture machine learning model for determining a type of facial gesture from a plurality of types of facial gestures.

The Analytics Engine sends the determined output to a computing device to perform an action based on the determined output (Act 306). According to various embodiments, the Analytics Engine detects a relationship between the user's current level of a particular type of mental state with respect to a threshold for the particular type of mental state. The Analytics Engine identifies at least one input command that corresponds to the detected relationship between the user's current level of a particular type of mental state and the threshold. For example, the input command may include at least one of: (i) one or more instructions to initiate at least one of a notification and (ii) one or more instructions for one of (a) a reduction, (b) a minimization and (c) an elimination of presentation of one or more notifications on the computing device. The Analytics Engine sends the input command to the computing device.

According to various embodiments, the detected relationship between the user's current level of the particular type of mental state and the threshold may be based on an indication of the user's current level of focus being higher than a focus threshold (e.g. or attention being higher than an attention threshold). The input command may be a trigger to initiate a reduction of presentation of one or more notifications on the computing device to assist the user in maintaining the current level of high focus. The input command may be (or may further include) a trigger to initiate presentation of a color and/or a light on a portion of the set of headphones to signal to any individual possibly near the user to not disturb the user during the current level of high focus. According to various embodiments, the headphones could then display a 'do-not-disturb' signal which for instance could be a red light. Similarly, according to various embodiments, the detected relationship between the user's current level of attention being lower than an attention threshold. The input command may be a trigger to initiate the presentation of a color and/or a light on a portion of the set of headphones to signal that the user is open be being disturbed, for instance a green light.

According to various embodiments, the detected relationship between the user's current level of the particular type of mental state and the threshold may be based on an indication of the user's current level of mental fatigue being higher than a mental fatigue threshold. The input command may be a trigger to initiate presentation of one or more notifications to prompt the user to perform at least one physical action to assist the user in alleviating the current level of fatigue (e.g. "you seem tired, you should get up and walk around"). A physical action may be standing up and/or walking and/or consuming coffee/caffeine, stretching, breathing, doing yoga, changing task, and/or another type of mental break and physical movement/exercise. In another embodiment the notification may prompt the user to perform at least one mental action such as meditation, mindfulness, napping, and/or any other type of mental action which may rejuvenate the user. In another embodiment, which can be useful if a user if performing a potentially dangerous task (e.g. like driving a truck or a forklift or piloting a plane) if the user's current level of mental fatigue is significantly higher than a mental fatigue threshold, the input command may trigger the presentation of one or more notifications to the user or to the user's coworkers or foreman to indicate that the user may not be fit for duty at the moment and needs a break.

According to various embodiments, the determined output may be sent through a dynamic filter (such as a Kalman filter) before it is sent back to a computing device. Determined output may be based on a determined facial gesture. The Analytics Engine identifies an interaction that maps to the determined type of facial gesture and further identifies an input command that corresponds to the interaction. The Analytics Engine sends the input command to the computing device that is associated with the headphones. It is understood that a respective interaction comprises as type of user input represented by a respective occurrence of a facial gesture.

According to various embodiments, a type of facial gesture may be a sequence of facial gestures represented in extracted EMG features, whereby the sequence of facial gestures may map to an interaction of an attempt to match a passcode. The Analytics Engine may determine that the sequence of facial gestures matches a pre-defined passcode. Based on the sequence of facial gestures matching the passcode, the Analytics Engine sends output to the computing device indicating an instance of verification of an identity associated with the passcode. In certain scenarios it may be advantageous for a user to be able to enter a passcode without being observed typing or entering a passcode into a smartphone, tablet, laptop, or desktop computer. In such scenarios it may be advantageous for a user to be able to use a facial gesture that may be invisible or not noticeable to others, but that the Analytics Engine may determine matches a certain pattern. Further, the signatures of each facial gesture can differ slightly from person to person, so the variations in the signals received from one user's jaw clench may differ from another user's jaw clench; those variations could also be used to create a sort of facial gesture fingerprint, so that even if a different user completed the correct sequence of facial gestures, the Analytics Engine would determine that it is not the right passcode.

As shown in the flowchart 308 of FIG. 3B, the Analytics Engine receives data based on voltages generated in response to detection one or more jaw movements (Act 310). The Analytics Engine extracts features from the received data to generate determined output that corresponds to the one or more jaw movements (Act 312).

The Analytics Engine sends a command to a computing device to perform an input command pre-defined as being selected via occurrence of the user's jaw movements (Act 314). The computing device may be associated with the set of headphones worn by the user and be the same computing device that sent the electrode data to the Analytics Engine. For instance, the computing device may be the user's smartphone that is connected to the headphones via Bluetooth connection, and the jaw movement (e.g. a left-right-left jaw wiggle) may be associated with an input command (e.g. play/pause music) on the user's smartphone. In other embodiments, the computing device may be a different device than the one that sent the electrode data to the Analytics Engine. For example, the computing device that sent the electrode data to the Analytics Engine may be the user's smartphone running an application for communicating with the headphones and the computing device that receives the command may be a personal computer or computer tablet. In various embodiments, the smartphone may receive the command from the Analytics Engine and relay the command to the personal computer or computer tablet. For instance, the computing device may be the user's tablet that is connected to the headphones via Bluetooth connection, and the jaw movement (e.g. a forward jaw jutting) may be associated with an input command intended for execution on the user's desktop computer (e.g. save file). In various embodiments the smartphone may receive the command from the Analytics Engine and relay the command to the headphones. For instance, if the command from the Analytics Engine is to lower volume on the headphones and/or to turn on the do-not-disturb light.

Figure 4:
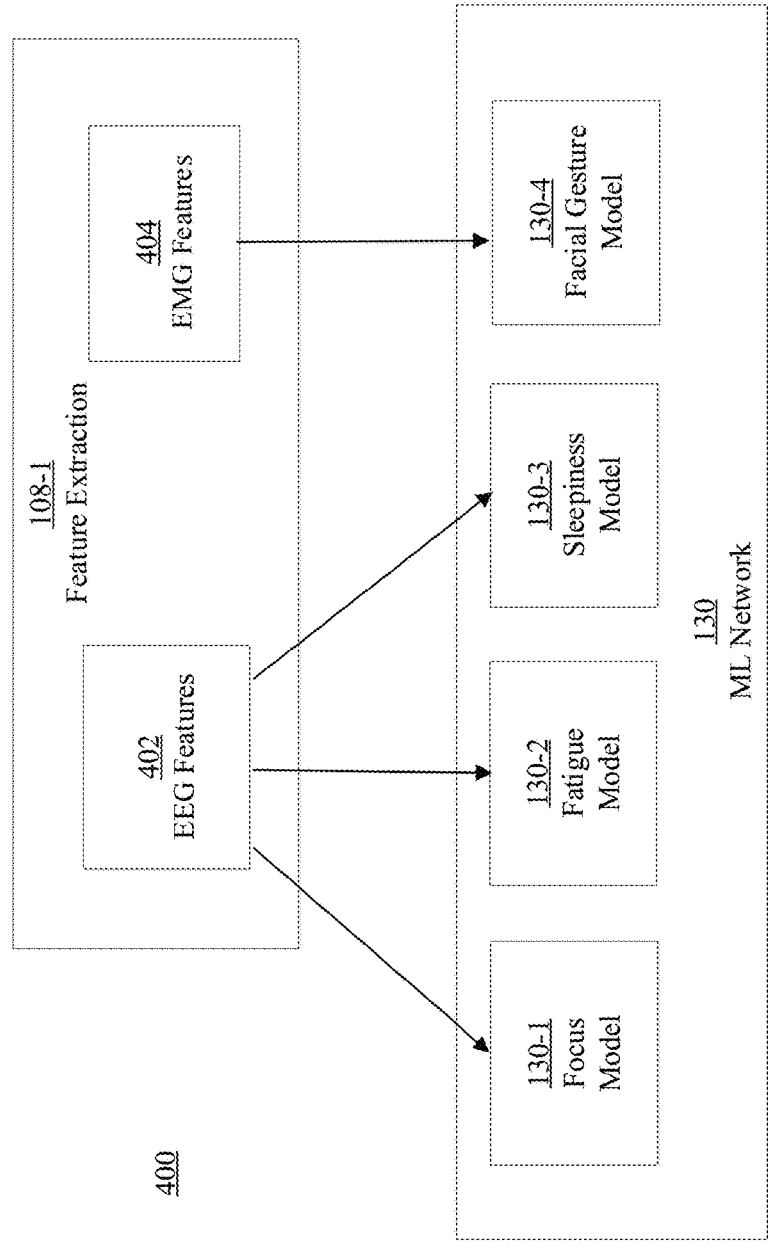
FIG. 4 is a diagram illustrating an exemplary environment in which some embodiments may operate.

As shown in diagram 400 of FIG. 4, the machine learning network 130 may include various types of machine learning models for determining a user's current level of focus 130-1, a current level of fatigue 130-2, current level sleepiness 130-3 and a type of facial gesture performed by the user 130-4. The Analytics Engine may deploy an instance of each model 130-1, 130-2, 130-3, 130-4 for each different user. In various embodiments, the Analytics Engine may also deploy an instance of each model that is generalized to work on different users. In various embodiments, the Analytics Engine may also deploy a hybrid instance of each model that contains both generalized models for use across different users and personalized models that customize the Model for a particular user. The electrodes on the headphones may continually detect EEG signals while the user wears the set of headphones. Data based on the EEG signals are continually sent to the Analytics Engine, which utilizes the data associated with EEG signals for the respective focus, fatigue, and sleepiness models 130-1, 130-2, 130-3. It is understood that the various types of machine learning models 130-1, 130-2, and 130-3 are not limited to the mental states of focus, fatigue and sleepiness. Rather, the various types of machine learning models may include machine learning models for other various types of mental states, cognitive states, attentive states, and/or arousal states, for instance focus, attention, distraction, cognitive load, fatigue, curiosity, certainty, doubt, mind wandering, sleepiness, admiration, adoration, aesthetic appreciation, amusement, anger, anxiety, awe, awkwardness, boredom, calmness, confusion, craving, disgust, empathic pain, entrancement, excitement, fear, horror, happiness, interest, joy, nostalgia, relief, romance, sadness, satisfaction, sexual desire, and/or surprise. The electrodes may continually detect changes in voltage while the user wears the set of headphones. In various embodiments, data based on the voltage signals are continually sent to the Analytics Engine, which uses the data associated with the voltage signals, extracts features from those signals, and uses them for the EEG Models (e.g. Focus 130-1, 130-2, 130-3), the EMG Models (e.g. Facial Gesture Model 130-4), for ECG models (e.g. heartrate), for Respiration models (e.g. breathing rate), and combinations thereof. In various embodiments the voltages detected are not just EEG or EMG signals but can include signals from other electrical processes in the body, such as ECG signals. In various embodiments, the different models (e.g. 130-1, 130-2, 130-3, and 130-4) may additionally take input from other data sources. In various embodiments, the headphones may have other types of sensors integrated into them or that are associated to them, whose data could be used by the Analytics Engine to extract additional features, incorporate them into the machine learning models, and improve the models. In various embodiments there may be other sensors associated with the headphones (e.g. integrated into the headphones directly or connected to the same computing device ((e.g. smartphone or tablet)) as the headphones, or connected to the headphones themselves), such as functional near infrared (fNIR) sensors that can detect changes in blood oxygenation and blood volume related to human brain function, magnetoencephalogic sensors that can detect small magnetic fields produced in the brain, or ultrasound transducer and sensor systems, heart rate sensors that can detect changes in heart rate or heart rate variability, blood oximeter sensor that can detect changes in blood, respiration sensors that can detect the respiration rate or respiration rate variability. In various embodiments signals from the different types of sensors are hybridized by the Analytics Engine Platform. For instance, the Facial Gesture Model 130-4 may additionally take input from a Gyroscope and/or Accelerometer associated with the headphones. The Gyroscope and/or Accelerometer may be located in the Headphones themselves and/or may be located on a device associated with the Headphones, such as the user's cell phone.

According to various embodiments, feature extraction from the EEG signal data includes extracting features 402, such as powerb and features, coherence features and power ratio features. The Analytics Engine extracts powerband features by doing a power spectral density analysis by first decomposing the signal into distinct frequency bands, like the alpha (8-12 hz), beta (12-30 Hz, theta (4-8 hz), gamma (30-100 Hz), and/or Delta (1-4 hz) frequency bands for each respective electrode expressed typically in Volts' per Hertz. This decomposition can be done with a Fourier transform, such as a Fast Fouriet Transform (FFT). Then the Analytics squares the magnitude of the FFT, resulting in the power spectral density of each frequency band. The Analytics Engine then determines a sum or average of the power densities of the identified alpha, beta, theta and gamma waves over a certain window.

The Analytics Engine extracts coherence features that represent how respective signals from different electrodes correspond to each other. Coherence features are based on comparisons of powerband data from respective pairs of electrodes. The comparisons are performed to determine a degree of similarity between the corresponding electrodes with respect to each compared power band (e.g. alpha, beta, theta, delta, and/or gamma). In some embodiments higher levels of coherence may between corresponding electrodes may indicate a higher signal to noise ratio. In addition, the Analytics Engine extracts power ratio features for representing ratios between power band features. The Analytics Engine feeds the extracted features into one or more of the respective differing types of mental state models 130-1, 130-2, 130-3 and sends determined output from each model back to the computing device(s) associated with the headphones.

According to one or more embodiments, the electrodes on the headphones may continually detect EMG signals generated when the user performs various facial muscle movements while wearing the set of headphones. Data based on the EMG signals are continually sent to the Analytics Engine, which utilizes the data associated with EMG signals for the facial gesture model 130-4. The Analytics Engine extracts features 404 for the for the facial gesture model 130-4 from the data associated with EMG signals. In various embodiments the Analytics Engine extracts features 404 from other data sources as well, for instance, from a Gyroscope and/or Accelerometer associated with the headphones. The Gyroscope and/or Accelerometer may be located in the Headphones themselves and/or may be located on a device associated with the Headphones, such as the user's cell phone. Accordingly, the Facial Gesture Model may be able to discern certain types of Facial Gestures that include both a movement of muscles within the face/head/neck as well as movement of the head or body as well. For instance, a head turn may activate muscles in the neck such as the sternocleidomastoid muscle which may produce an EMG signal that is detected by the headphones and used by the Analytics Engine using extracted EMG Feature 404, and the Facial Gesture Model 130-4 to determine that the user has turned their head; by combining the EMG Features 404 with Accelerometer Features and with Gyroscopic Features that are extracted by the Analytics Engine 404, and using those Features in the Facial Gesture Model 130-4, the accuracy, consistency, and/or speed of the Facial Gesture Model may be improved.

Figure 5:
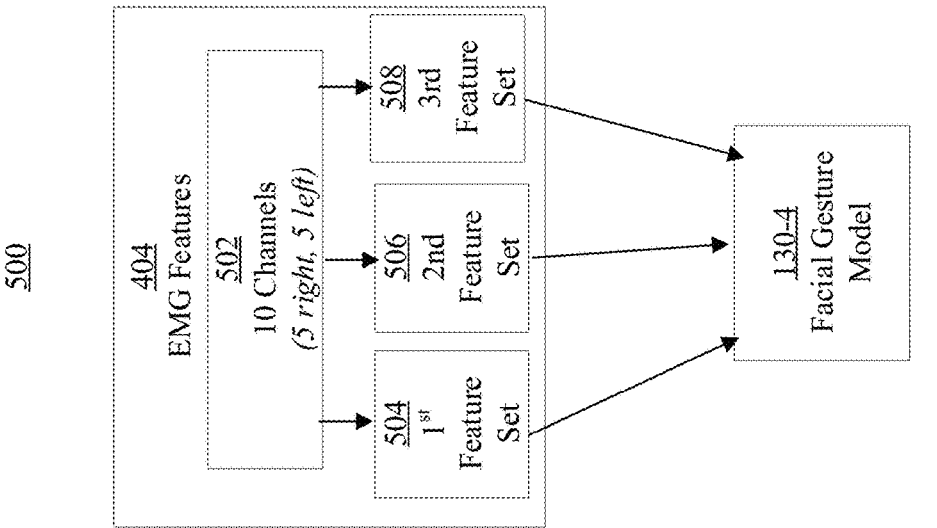
FIG. 5 is a diagram illustrating an exemplary environment in which some embodiments may operate.

As shown in diagram 500 of FIG. 5, a defined number of channels 502 may be associated with a left portion of the set of headphones and a defined number of channels may be associated with a right portion of the set of headphones. For example, the facial gesture model 130-4 may be based on three sets of features 504, 506, 508 where each feature set receives data from channels 502 that are associated with the electrodes on the headphones. Each channel may be associated with a particular electrode. For example, in one embodiment, five electrodes on the right portion of the headphones may be associated with a first set of corresponding five channels and the five electrodes on the left portion of the headphones may be also be associated with a second set of corresponding five channels. As such, data based on each of the ten channels 502 may be fed into each of feature sets in the three feature sets 504, 506, 508 (i.e. the ten channels for the $1^{st}$ Feature Set, ten channels for the $2^{nd}$ Feature Set, ten channels for the $3^{rd}$ Feature Set).

According to various embodiments, the $1^{st}$ Feature Set 504 includes 10 channels of the average amplitude of the voltage over a 1 second window from each of the electrodes (e.g. the DC-offset, or how much the average of the absolute value of the signal deviates from zero. Which, the $2^{nd}$ Feature Set 506 includes 10 channels of a high frequency (e.g. 30-50 hz) powerband from each of the electrodes, and the $3^{rd}$ Features Set 508 includes 10 channels of low frequency (e.g. 9-12 hz) powerband from each of the electrodes. Electrode data may be initially captured as a raw signal, sampled at 300 Hz by one or more processing units on the headphones and then split into two different frequency bands (e.g. frequency band 9-12 hz and 30-50 hz). In various embodiments, there may be one or more frequency bands used, including 1, 2, 3, 4, 5, 6, 7, 8, 9, 10, 11, 12, 13, 14, 15, or more frequency bands used. The frequency bands may also span larger or smaller windows, for example 5-20 hz, 6-18 hz, 8-16 hz, 10-30 hz, 15-25 hz, 20-30 hz, 20-80 hz, 25-75 hz, 30-70 hz, 35-65 hz, 40-60 hz, 45-65 hz, 10-100 hz, and many others. For example, data sent from the headphones represents changes in voltages every $\frac{1}{300}^{th}$ of a second for each of the 10 channels. Each second of raw signal data is aggregated into an individual signal file. Each signal file includes data for the ten channels 502 for the three feature sets 504, 506, 508. Embodiments described herein are not limited to a time window of one second for each signal file, so the time windows may be exactly or approximately 0.1 seconds, 0.2 seconds, 0.3 seconds, 0.4 seconds, 0.5 seconds, 0.6 seconds, 0.7 seconds, 0.8 seconds, 0.9 seconds, 1 second, 1.1 seconds, 1.2 second, 1.3 second, 1.4 seconds, 1.5 seconds, 1.6 seconds, 1.7 seconds, 1.8 seconds, 1.9 seconds, 2 seconds, or more. The data windows may be sequential or may be overlapping. Further the sampling rate may be exactly or approximately 200 hz, 225 hz, 250 hz, 275 hz, 300 hz 325 hz, 350 hz, 375 hz, 400 hz, 425 hz, 450 hz, 475 hz, 500 hz, 525 hz, 550 hz, 575 hz, 600 hz, or more.

According to various embodiments, the facial gesture model 130-4 may be based, at least in part, on linear discriminate analysis (LDA) which for instance includes a 30-dimensional model (based on 3 features over 10 channels) and projects all the points from the 3 feature sets into n-dimensional space (whereby n represents a number of classes minus 1). The facial gesture model 130-4 then implements a k-nearest neighbors (KNN) algorithm to identify a particular facial muscle gesture. For example, if a point is projected into the n-dimensional space and the new point's 5 nearest neighboring points (e.g. k=5) were previously identified as jaw clench interactions, then the new point is identified as a jaw clench interaction as well. The hyperparameter "k" is not limited to the number 5, and in various embodiments is 2, 3, 4, 5, 6, 7, 8, 9, 10, 11, 12, 13, 14, 15, 16, 17, 18, 19, 20, or more.

It is understood that various embodiments described herein may perform a training phase. If there is no model for a particular user, software on the computing device associated with a set of headphones currently being worn by the particular user instructs the particular user to perform a series of one or more different types of training facial gestures. For instance, the user may be prompted to clench their jaw 10 times in a row, then may be prompted to click their teeth 10 times in a row, then may be prompted to nod their head 10 times in a row, then may be prompted to wink 10 times in a row, then may be asked to do 'no facial gesture' 10 times in a row. Because the user is prompted to perform each of these gestures at a certain time, the data from the headphones can be labeled automatically and the LDA+ KNN Facial Gesture Model 130-4 can be trained. Electrode data from the training of facial muscle gestures are mapped to pre-defined interactions and the Analytics Engine trains an instance of each model 130-4 for each particular user based on the electrode data mappings. Once a model has been trained and/or exists, the system will enter a prediction mode to determine what facial gesture the user is performing. According to various embodiments, the particular user may select which type of facial gesture corresponds to a desired interaction. According to various embodiments a desired interaction may be automatically or predetermined to be associated with a specific facial gesture.

Figure 6A:
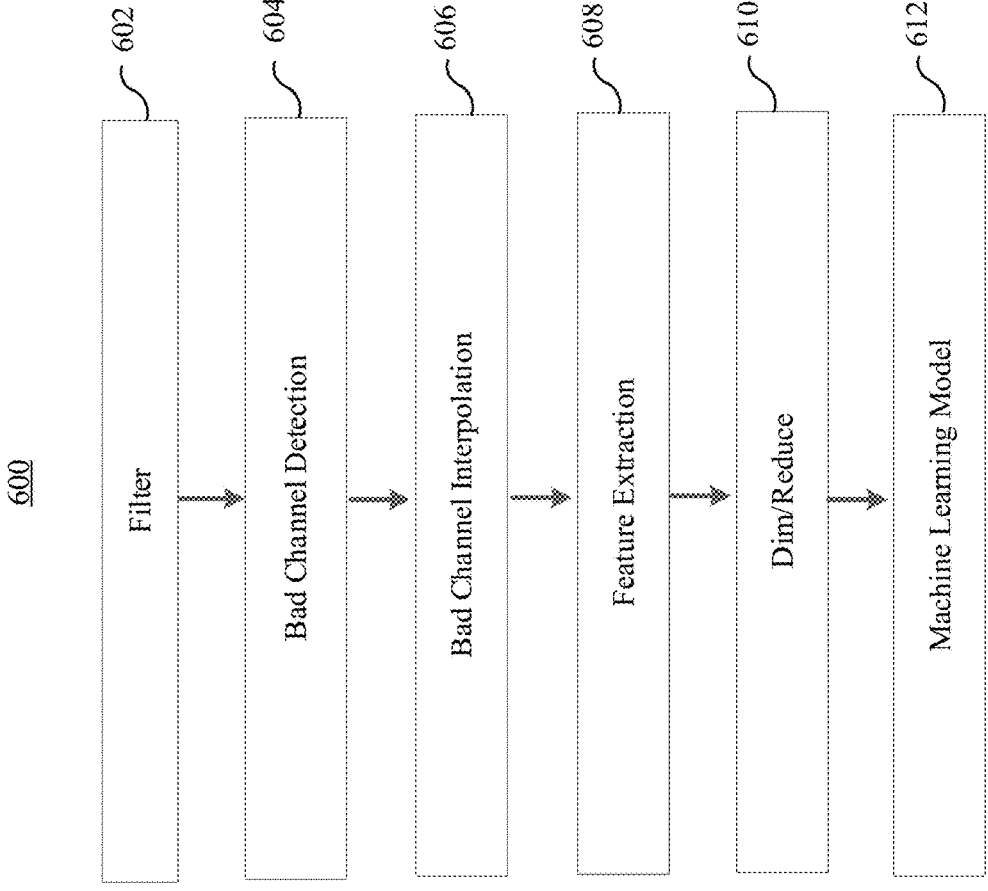
FIG. 6A is a diagram illustrating an exemplary method that may be performed in some embodiments.
Figure 6B:
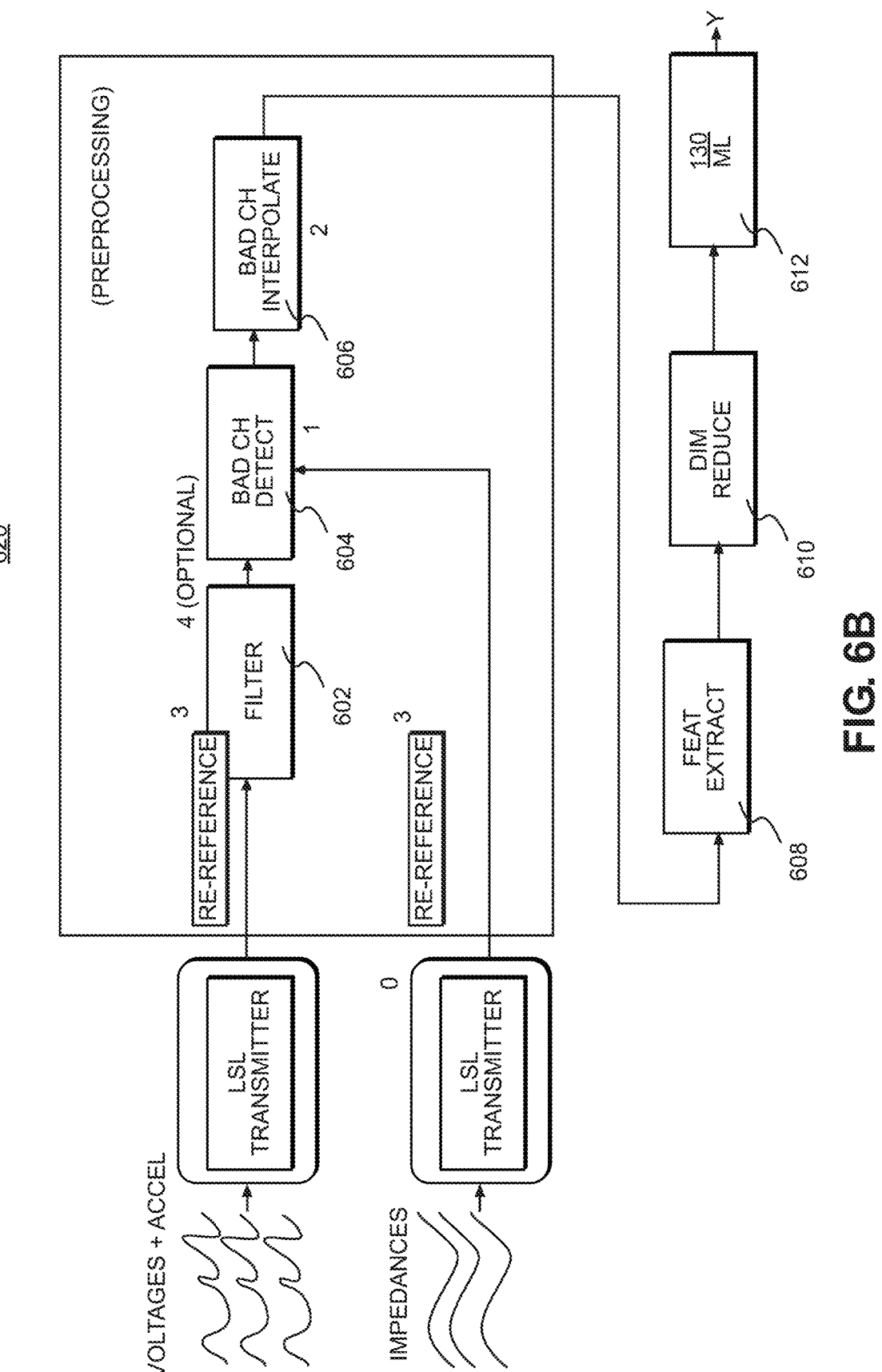
FIG. 6B is a diagram illustrating an exemplary environment in which some embodiments may operate.

As shown in flowchart 600 of FIG. 6A, and further illustrated in a diagram 620 of FIG. 6B, a facial gesture architecture implemented by the Analytics Engine receives incoming data that represents voltages and impedances from one or more LSL (lab streaming layer) transmitters from the headphones. The voltages are filtered to remove voltage above and below various frequency thresholds (Act 602). The voltages are also filtered to remove 60 hz noise.

The Analytics Engine performs a bad channel detection algorithm on the filtered voltages (Act 604). The Analytics Engine flags data from a particular electrode in a corresponding channel as bad data based on whether the data meets one or more impedance criteria.

The Analytics Engine then performs an interpolation algorithm with respect to each flagged bad channel (Act 606). The interpolation algorithm improves each flagged bad channel by replacing the bad channel data with a weighted average of the channels that were not flagged during bad channel detection.

The Analytics Engine extracts features from the data from the good channels and the improved bad channels (Act 608). The Analytics Engine calculates spectral power estimates for each channel. For example, the analytics engine calculates spectral power estimates for a one second of data that window may have been generated when the user wore the headphones and performed a particular facial gesture. The window may be exactly or approximately 0.1 seconds, 0.2 seconds, 0.3 seconds, 0.4 seconds, 0.5 seconds, 0.6 seconds, 0.7 seconds, 0.8 seconds, 0.9 seconds, 1 second, 1.1 seconds, 1.2 second, 1.3 second, 1.4 seconds, 1.5 seconds, 1.6 seconds, 1.7 seconds, 1.8 seconds, 1.9 seconds, 2 seconds, or more. The data windows may be sequential or may be overlapping. In addition, the Analytics Engine also splits data from each one second window into a plurality of segments. Each segment of channel data may correspond to a signal during a 50-millisecond duration. The duration of the segments may be exactly or approximately 10-milliseconds, 20 milliseconds, 30 milliseconds, 40 milliseconds, 50 milliseconds, 60 milliseconds, 70 milliseconds, 80 milliseconds, 90 milliseconds, 100 milliseconds, 110 milliseconds, 120 milliseconds, 130 milliseconds, 140 milliseconds, 150 milliseconds, 160 milliseconds, 170 milliseconds, 180 milliseconds, 190 milliseconds, 200 milliseconds, 210 milliseconds, 220 milliseconds, 230 milliseconds, 240 milliseconds, 250 milliseconds, or more. Each segment may be sequential or in other cases overlapping with the previous segment. The Analytics Engine estimates the power of oscillations in each 50-millisecond segment of channel data which provides an estimate of how signal power varies over the course of a gesture. Further features may be derived using linear or non-linear combinations of individual channel features. Different facial gestures may be identified both the spectral power features associated with the one second window, and also by the gesture-specific patterns of spectral power contained within the 50-millisecond segments as learned by the facial gesture model 130-4. Various embodiments are not limited to implementing only one second time windows or 50-millisecond segments. In various embodiments, each feature for the facial gesture model 130-4 may be based on a horizontal slice across spectrogram (i.e. a time-frequency plot). A spectrogram slice may include a row of pixels from a respective spectrogram. Each channel may have its own spectrogram slice and each pixel in a channel's spectrogram slice represents an amplitude of an oscillation of a signal at a given frequency at a given point in time. Spectrogram slices may be re-assembled in linear or nonlinear combinations of the slices from individual channels.

The Analytics Engine may then perform a dim/reduce algorithm to reduce the number of extracted features by eliminating extracted features that are redundant via principle component analysis (Act 610). The Analytics Engine feeds the output from the dim/reduce algorithm into the facial gesture model 130-4, which may be based on one or more non-linear classifiers, such as a Random forest network and/or kernel support vector machine (Act 612).

Figure 7:
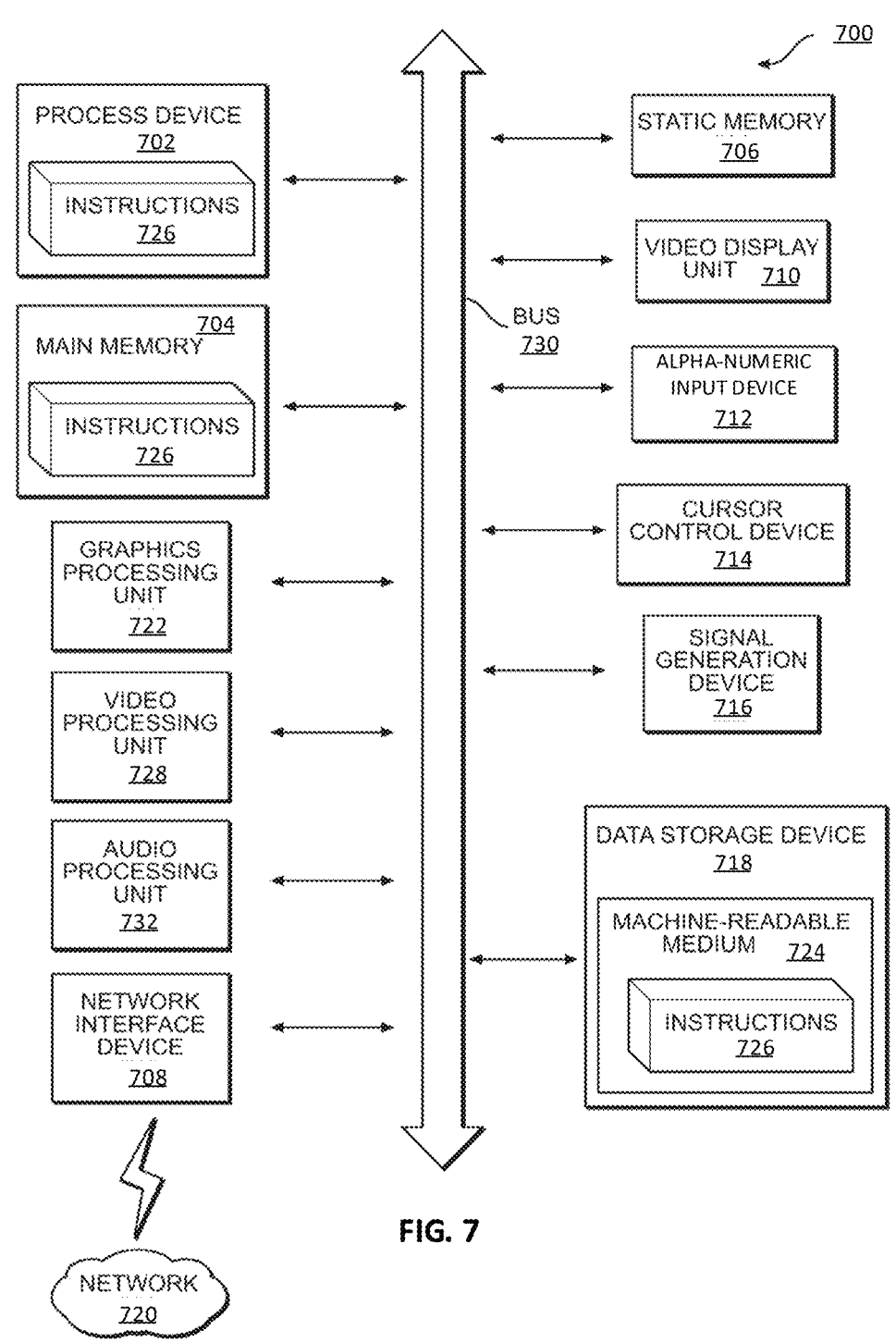
FIG. 7 is a diagram illustrating an exemplary environment in which some embodiments may operate.

FIG. 7 illustrates an example machine of a computer system within which a set of instructions, for causing the machine to perform any one or more of the methodologies discussed herein, may be executed. In alternative implementations, the machine may be connected (e.g., networked) to other machines in a LAN, an intranet, an extranet, and/or the Internet. The machine may operate in the capacity of a server or a client machine in client-server network environment, as a peer machine in a peer-to-peer (or distributed) network environment, or as a server or a client machine in a cloud computing infrastructure or environment.

The machine may be a personal computer (PC), a tablet PC, a set-top box (STB), a Personal Digital Assistant (PDA), a cellular telephone, a web appliance, a server, a network router, a switch or bridge, or any machine capable of executing a set of instructions (sequential or otherwise) that specify actions to be taken by that machine. Further, while a single machine is illustrated, the term "machine" shall also be taken to include any collection of machines that individually or jointly execute a set (or multiple sets) of instructions to perform any one or more of the methodologies discussed herein.

The example computer system 700 includes a processing device 702, a main memory 704 (e.g., read-only memory (ROM), flash memory, dynamic random access memory (DRAM) such as synchronous DRAM (SDRAM) or Rambus DRAM (RDRAM), etc.), a static memory 706 (e.g., flash memory, static random access memory (SRAM), etc.), and a data storage device 718, which communicate with each other via a bus 730.

Processing device 702 represents one or more general-purpose processing devices such as a microprocessor, a central processing unit, or the like. More particularly, the processing device may be complex instruction set computing (CISC) microprocessor, reduced instruction set computing (RISC) microprocessor, very long instruction word (VLIW) microprocessor, or processor implementing other instruction sets, or processors implementing a combination of instruction sets. Processing device 702 may also be one or more special-purpose processing devices such as an application specific integrated circuit (ASIC), a field programmable gate array (FPGA), a digital signal processor (DSP), network processor, or the like. The processing device 702 is configured to execute instructions 726 for performing the operations and steps discussed herein.

The computer system 700 may further include a network interface device 708 to communicate over the network 720. The computer system 700 also may include a video display unit 710 (e.g., a liquid crystal display (LCD) or a cathode ray tube (CRT)), an alphanumeric input device 712 (e.g., a keyboard), a cursor control device 714 (e.g., a mouse), a graphics processing unit 722, a signal generation device 716 (e.g., a speaker), graphics processing unit 722, video processing unit 728, and audio processing unit 732.

The data storage device 718 may include a machine-readable storage medium 724 (also known as a computer-readable medium) on which is stored one or more sets of instructions or software 726 embodying any one or more of the methodologies or functions described herein. The instructions 726 may also reside, completely or at least partially, within the main memory 704 and/or within the processing device 702 during execution thereof by the computer system 700, the main memory 704 and the processing device 702 also constituting machine-readable storage media.

In one implementation, the instructions 726 include instructions to implement functionality corresponding to the components of a device to perform the disclosure herein. While the machine-readable storage medium 724 is shown in an example implementation to be a single medium, the term "machine-readable storage medium" should be taken to include a single medium or multiple media (e.g., a centralized or distributed database, and/or associated caches and servers) that store the one or more sets of instructions. The term "machine-readable storage medium" shall also be taken to include any medium that is capable of storing or encoding a set of instructions for execution by the machine and that cause the machine to perform any one or more of the methodologies of the present disclosure. The term "machine-readable storage medium" shall accordingly be taken to include, but not be limited to, solid-state memories, optical media and magnetic media.

Some portions of the preceding detailed descriptions have been presented in terms of algorithms and symbolic representations of operations on data bits within a computer memory. These algorithmic descriptions and representations are the ways used by those skilled in the data processing arts to most effectively convey the substance of their work to others skilled in the art. An algorithm is here, and generally, conceived to be a self-consistent sequence of operations leading to a desired result. The operations are those requiring physical manipulations of physical quantities. Usually, though not necessarily, these quantities take the form of electrical or magnetic signals capable of being stored, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the above discussion, it is appreciated that throughout the description, discussions utilizing terms such as "identifying" or "determining" or "executing" or "performing" or "collecting" or "creating" or "sending" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage devices.

The present disclosure also relates to an apparatus for performing the operations herein. This apparatus may be specially constructed for the intended purposes, or it may comprise a general purpose computer selectively activated or reconfigured by a computer program stored in the computer. Such a computer program may be stored in a computer readable storage medium, such as, but not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions, each coupled to a computer system bus.

Various general purpose systems may be used with programs in accordance with the teachings herein, or it may prove convenient to construct a more specialized apparatus to perform the method. The structure for a variety of these systems will appear as set forth in the description above. In addition, the present disclosure is not described with reference to any particular programming language. It will be appreciated that a variety of programming languages may be used to implement the teachings of the disclosure as described herein.

The present disclosure may be provided as a computer program product, or software, that may include a machine-readable medium having stored thereon instructions, which may be used to program a computer system (or other electronic devices) to perform a process according to the present disclosure. A machine-readable medium includes any mechanism for storing information in a form readable by a machine (e.g., a computer). For example, a machine-readable (e.g., computer-readable) medium includes a machine (e.g., a computer) readable storage medium such as a read only memory ("ROM"), random access memory ("RAM"), magnetic disk storage media, optical storage media, flash memory devices, etc.

In the foregoing disclosure, implementations of the disclosure have been described with reference to specific example implementations thereof. It will be evident that various modifications may be made thereto without departing from the broader spirit and scope of implementations of the disclosure as set forth in the following claims. The disclosure and drawings are, accordingly, to be regarded in an illustrative sense rather than a restrictive sense.

What is claimed is:

1. A computer-implemented method, comprising:
receiving one or more signal files of data based on voltages detected by one or more electrodes on a set of headphones worn by a user, wherein at least one of the electrodes comprises a first electrode for detecting both an EEG signal and an EMG signal;
extracting features from the received data and feeding the extracted features into one or more machine learning models to generate a determined output that corresponds to at least one of a current mental state of the user and a type of one or more facial gestures performed by the user; and
sending the determined output to a computing device to perform an action based on the determined output;
wherein extracting features comprises:
extracting one or more EEG features from the received data based at least on EEG signals detected by the first electrode;
feeding at least one of the extracted EEG features into at least one of a first machine learning model for determining a current level of focus of the user, a second machine learning model for determining a current level of attentiveness of the user and a third machine learning model for determining a current level of cognitive load of the user;
extracting EMG features from the received data based at least on EMG signals detected by the first electrode; and
feeding one or more of the extracted EMG features into a facial gesture machine learning model for determining a type of facial gesture from a plurality of types of facial gestures.

2. The computer-implemented method as in claim 1, wherein each of the electrodes on the set of headphones being situated on a respective ear cuff cushion of the set of headphones.

3. The computer-implemented method as in claim 2, wherein each of the electrodes makes electrical contact to the user via a conductive textile of the set of headphones.

4. The computer-implemented method as in claim 1, wherein the determined output comprises at least one input command, wherein the input command includes at least one of, (i) one or more instructions to initiate at least one of a notification and (ii) one or more instructions for one of (a) a reduction, (b) a minimization and (c) an elimination of presentation of one or more notifications on the computing device; and
sending the input command to the computing device.

5. The computer-implemented method as in claim 1, wherein sending the determined output to a computing device to perform an action based on the determined output comprises:
detecting a relationship between a current level of a particular type of mental state of the user with respect to a threshold for the particular type of mental state;
identifying at least one input command that corresponds to the detected relationship between the current level of the particular type of mental state of the user and the threshold; and
sending the input command to the computing device.

6. The computer-implemented method as in claim 5, further comprising:
wherein the detected relationship between the current level of the particular type of mental state of the user and the threshold comprises: an indication of the current level of focus of the user being higher than a focus threshold; and
wherein the input command comprises a trigger to initiate a reduction of presentation of one or more notifications on the computing device to assist the user in maintaining the current level of high focus.

7. The computer-implemented method as in claim 6, wherein the input command further comprises a trigger to initiate presentation of a color on a portion of the set of headphones to signal to any individual possibly near the user to not disturb the user during the current level of high focus.

8. The computer-implemented method as in claim 5, further comprising:
wherein the detected relationship between the current level of the particular type of mental state of the user and the threshold comprises: an indication of the current level of mental fatigue of the user being higher than a mental fatigue threshold; and
wherein the input command comprises a trigger to initiate presentation of one or more notifications to prompt the user to perform at least one physical action to assist the user in alleviating the current level of mental fatigue.

9. The computer-implemented method as in claim 1, wherein the type of facial gesture includes a sequence of facial gestures represented in the one or more of the extracted EMG features, the sequence of facial gestures comprising an attempt to match a passcode; and
wherein sending the determined output to a computing device to perform an action based on the determined output comprises: determining that the sequence of facial gestures matches the passcode; and
based on the sequence of facial gestures matching the passcode, sending output to the computing device indicating an instance of verification of an identity associated with the passcode.

10. The computer-implemented method as in claim 9, wherein the type of facial gesture has one or more corresponding additional components;

wherein receiving one or more signal files comprises: receiving one or more signal files of data of one or more additional data type portions;

wherein extracting EMG features from the received data comprises: extracting additional features from the one or more additional data type portions;

feeding one or more of the extracted EMG features into a facial gesture machine learning model comprises: feeding the extracted additional features into the facial gesture machine learning model to generate a determined output that corresponds to the type of facial gesture performed by the user.

11. The computer-implemented method as in claim 10, comprises:

wherein the one or more additional data type portions comprises audio data based on sound detected by one or more microphones associated with the headphones; and wherein the additional features comprise audio features.

12. The computer-implemented method as in claim 10, comprises:

wherein the one or more additional data type portions comprises movement data based on at least one change in a physical orientation of a motion detector associated with the set of headphones;

wherein the additional features comprise movement features; and wherein the determined output corresponds to the type of facial gesture and a type of head movement.

13. The computer-implemented method as in claim 9, wherein sending the determined output to a computing device to perform an action based on the determined output comprises:

identifying an interaction that maps to the determined type of facial gesture;

identifying an input command that corresponds to the interaction; and sending the input command to the computing device.

14. The computer-implemented method as in claim 13, wherein the interaction comprises a prompt interaction from the user to the computing device; and wherein the input command comprises a trigger for initiation of a computing device mode in response to the prompt interaction from the user.

15. The computer-implemented method as in claim 14, wherein the prompt interaction comprises one of a request to enter into a wake mode and a request to enter into a sleep mode; and wherein the input command comprises one of a trigger for the computing device to enter into an awakened mode to monitor for an occurrence of at least one subsequent input command and a trigger for the computing device to enter into the sleep mode.

16. The computer-implemented method as in claim 1, further comprising:

wherein receiving data based on voltages detected by one or more electrodes on a set of headphones worn by the user comprises receiving data based on voltages generated in response to detection one or more jaw movements;

wherein extracting features comprises: extracting features from the received data to generate determined output that corresponds to the one or more jaw movements; and wherein sending the determined output to the computing device comprises: sending a command to the computing device to perform an input command pre-defined as being selected via the one or more jaw movements of the user detected by the one or more electrodes on the set of headphones worn by the user.

17. The computer-implemented method as in claim 1, further comprising:

prior to extracting features from the received data:

detecting whether one or more signal files of data from a respective electrode channel represent good channel data or bad channel data based on at least one or more impedance criteria; and based on said determination, removing the bad channel data and replacing the removed bad channel data with good data to create one or more improved channels, and wherein extracting features from the received data comprises: extracting features from at least one of the good channels and at least one of the improved channels.

18. A system comprising:

one or more processors; and a non-transitory computer readable medium storing a plurality of instructions, which when executed, cause the one or more processors to:

receive one or more signal files of data based on voltages detected by one or more electrodes on a set of headphones worn by a user, wherein at least one of the electrodes comprises a first electrode for detecting both an EEG signal and an EMG signal;

extract features from the received data and feeding the extracted features into one or more machine learning models to generate a determined output that corresponds to at least one of a current mental state of the user and a type of one or more facial gestures performed by the user; and send the determined output to a computing device to perform an action based on the determined output;

wherein extract features comprises:

extract one or more EEG features from the received data based at least on EEG signals detected by the first electrode;

feed at least one of the extracted EEG features into at least one of a first machine learning model for determining a current level of focus of the user, a second machine learning model for determining a current level of attentiveness of the user and a third machine learning model for determining a current level of cognitive load of the user;

extract EMG features from the received data based at least on EMG signals detected by the first electrode; and feed one or more of the extracted EMG features into a facial gesture machine learning model for determining a type of facial gesture from a plurality of types of facial gestures.

19. The system of claim 18, wherein receiving data based on voltages detected by one or more electrodes on a set of headphones worn by the user comprises receiving data based on voltages generated in response to detection one or more jaw movements;

wherein extracting features comprises: extracting features from the received data to generate determined output that corresponds to the one or more jaw movements; and wherein sending the determined output to the computing device comprises: sending a command to the computing device to perform an input command pre-defined as being selected via the one or more jaw movements of the user detected by the one or more electrodes on the set of headphones worn by the user.

20. A computer program product comprising a non-transitory computer-readable medium having a computer-readable program code embodied therein to be executed by one or more processors, the program code including instructions to:

receive one or more signal files of data based on voltages detected by one or more electrodes on a set of headphones worn by a user, wherein at least one of the electrodes comprises a first electrode for detecting both an EEG signal and an EMG signal;

extract features from the received data and feeding the extracted features into one or more machine learning models to generate a determined output that corresponds to at least one of a current mental state of the user and a type of one or more facial gestures performed by the user; and send the determined output to a computing device to perform an action based on the determined output;

wherein extract features comprises:

extract one or more EEG features from the received data based at least on EEG signals detected by the first electrode;

feed at least one of the extracted EEG features into at least one of a first machine learning model for determining a current level of focus of the user, a second machine learning model for determining a current level of attentiveness of the user and a third machine learning model for determining a current level of cognitive load of the user;

extract EMG features from the received data based at least on EMG signals detected by the first electrode; and feed one or more of the extracted EMG features into a facial gesture machine learning model for determining a type of facial gesture from a plurality of types of facial gestures.

* * * * *